US008790692B2

(12) United States Patent
Wang et al.

(10) Patent No.: US 8,790,692 B2
(45) Date of Patent: Jul. 29, 2014

(54) BREAK RESISTANT GEL CAPSULE

(75) Inventors: Haibo Wang, West Chester, OH (US); Dawn Downey, West Chester, OH (US); Lester David Fulper, Clearwater, FL (US)

(73) Assignee: Patheon Pharmaceuticals Inc., Cincinnati, OH (US)

( * ) Notice: Subject to any disclaimer, the term of this patent is extended or adjusted under 35 U.S.C. 154(b) by 390 days.

(21) Appl. No.: 12/877,653

(22) Filed: Sep. 8, 2010

(65) Prior Publication Data

US 2011/0097397 A1 Apr. 28, 2011

Related U.S. Application Data

(60) Provisional application No. 61/240,866, filed on Sep. 9, 2009, provisional application No. 61/256,626, filed on Oct. 30, 2009.

(51) Int. Cl.
*A61K 9/48* (2006.01)
*A61J 3/07* (2006.01)

(52) U.S. Cl.
CPC .................................... *A61J 3/071* (2013.01)
USPC ........................................................ 424/454

(58) Field of Classification Search
None
See application file for complete search history.

(56) References Cited

U.S. PATENT DOCUMENTS 525,844 A 9/1894 Hobbs
525,845 A 9/1894 Hobbs
1,536,219 A 5/1925 Johnson
2,718,980 A 5/1955 Strom
5,769,267 A 6/1998 Duynslager et al.
2007/0036830 A1 2/2007 Vanquickenborne et al.
2007/0048368 A1 3/2007 Dong et al.

FOREIGN PATENT DOCUMENTS

EP 0 180 543 5/1986

OTHER PUBLICATIONS

Stegemann (Capsulgel Hard gelatin capsules today and tomorrow 2002 2nd edition; 23 pages).*
Podczeck (Pharmaceutical capsules 2004, Pharmaceutical Press pp. 80, 83, 85, 91 and 92: 5 pages total).*
International Search Report dated May 23, 2011 (3 pgs.).

* cited by examiner

*Primary Examiner* — Ernst V Arnold
(74) *Attorney, Agent, or Firm* — Fulbright & Jaworski LLP; Scott D. Rothenberger

(57) ABSTRACT

A gelatin capsule is disclosed that is designed to impart less tensile stress on the component parts when it is in the closed position and experiences less spontaneous breakage particularly when fill with hygroscopic liquids. The gelatin capsule comprises a cap portion and a body portion. The cap portion includes an annular ring and the body portion includes an annular groove. Together, the annular ring and the annular groove comprise a locking ring, which are designed to reduce the capsule cap and body contact force and stress raisers. The invention includes a cap locking ring inner diameter that is same as body locking ring outer diameter or slightly smaller to make the contacting force at the locking ring lower than current capsule designs. The body portion also includes a tapered ring configured such that, in the closed position the rim of the body portion does not contact the cap portion.

32 Claims, 23 Drawing Sheets

Moisture gradient across capsule shell wall when filled with hygroscopic material

Gelatin plasticity gradient across capsule shell wall when filled with hygroscopic material Stress distribution across capsule shell wall when filled with hygroscopic material

BREAK RESISTANT GEL CAPSULE

CROSS REFERENCE TO RELATED APPLICATIONS

This application claims benefit of U.S. Provisional Patent Application No. 61/240,866, filed Sep. 9, 2009, and U.S. Provisional Patent Application No. 61/256,626, filed Oct. 30, 2009, entitled "Break Resistant Gel Capsule", the contents of which are both incorporated in their entirety herein by reference.

FIELD OF THE INVENTION

The present invention is directed to a gelatin capsule that is designed to impart less tensile stress on the component parts when it is in the closed position and therefore experiences less spontaneous breakage particularly when filled with hygroscopic liquids.

BACKGROUND OF THE INVENTION

As the popularity of liquid-filled hard capsules (LFHC) increases, formulators are becoming more interested in ways to evaluate the compatibility for their formulations with the capsule shell, particularly in the pharmaceutical arena, where it is sometimes necessary to use hygroscopic fill materials that can cause capsules to break. While breaks in capsules filled with powders can be a nuisance breakage of LFHCs is unacceptable since a single broken capsule can contaminate an entire package.

The theory behind capsule breakage is that hygroscopic fill materials pull water from the capsule shell. The shell then becomes brittle, making it less resistant to impact forces normally encountered during handling. While the inventors, during the course of their research identified the economic and commercial drawbacks of the discussed capsule breakage, they found that no systematic study has been performed to identify the causes of such breakage and identify methods to limit the waste.

Capsules consisting of telescopic parts have been known for a long time. U.S. Pat. No. 525,845 of 1894 describes a telescopic capsule, comprising a cap, having an annular constriction approximately in the middle and flares toward its open end. The capsule body is designed to be embraced by the annular constriction when the parts of the capsule are fitted together. This allegedly results in a good fit of the cap of the capsule on the body thereof.

In another capsule, such as is disclosed in U.S. Pat. No. 2,718,980, the capsule cap has on its inside an annular projection and an annular groove. The capsule body is also provided adjacent to its opening with an annular projection and an annular groove. A reliable seal between the cap and body of the capsule is allegedly ensured in that the projection and groove of one part of the capsule snap into the groove and projection of the other capsule part when these parts are pushed one into the other.

Both the capsule cap and the capsule body of the capsule described in the German Patent Specification 1,536,219 are formed with an annular constriction. When the two parts of the capsule are fitted one into the other, the convex annular bead formed on the inside of the capsule cap in conjunction with the constriction enters the annular constriction of the capsule body.

Capsules for containing medicaments are generally made today from hard gelatin in a dipping process. In this process, properly designed pins are dipped into an aqueous solution of gelatin and are subsequently withdrawn from the gelatin solution. When the gelatin has dried on the pin, the gelatin body is stripped from the pin and the resulting capsule part is cut to the desired length. In this practice it has been found that annular convex projections or concave recesses on the pin render the stripping of the gelatin body more difficult. Besides, it is almost impossible to obtain an airtight seal between the capsule cap and the rim of the capsule body when capsule parts are fitted together. This is due to the length tolerances of the capsule parts, particularly to the different distances between the rim and the annular recess of the capsule body. For a reliably fitting joint, the mating annular concave recesses or convex projections must interengage although this does not ensure an airtight seal and conventional wisdom has propagated the belief that the air-tight seal is mandatory for LFHC.

Therefore, early in the course of their investigations with LFHCs, the inventors recognized that the design of LFHC and the effect of hygroscopic fill materials was an important aspect to be considered in order to support the needs and uses required by LFHCs. As such a need exists to overcome the deficiencies of current LFHCs.

SUMMARY OF THE INVENTION

Without being held to any particular theory, the inventors of the present invention hypothesized that by identifying the stresses imparted on LFHCs upon filling with hygroscopic materials the stresses could be limited and the waste resulting from such breakage would be reduced.

The present invention is directed to a gelatin capsule that is designed to impart less tensile stress on the component parts when it is in the closed position and therefore experiences less spontaneous breakage particularly when filled with hygroscopic liquids. The gelatin capsule comprises a cap portion and a body portion. The cap portion includes an annular ring and the body portion includes an annular groove. Together, the annular ring and the annular groove comprise a locking ring. In one embodiment of the invention, the annular ring is narrower than the annular groove but the annular ring is higher than the depth of the annular groove. The body portion also includes a tapered ring configured such that, in the closed position the rim of the body portion does not contact the cap portion.

Therefore, in various exemplary embodiments, the invention comprises a gelatin capsule comprising a body portion and a cap portion. In some embodiments the body portion has an open top including a tapered rim, shoulder area and a closed rounded bottom. In these embodiments, the cap portion having a closed rounded top, a shoulder area and open bottom, the top portion dimensioned and configured to fit over the body portion to comprise a closed capsule. In some exemplary embodiments, the tapered rim is dimensioned and configured such that when the cap is secured, the rim does not contact the cap portion. In some exemplary embodiments, the body portion further includes a first part of a locking ring comprising an annular groove around the circumference of the body portion. In these exemplary embodiments, the cap portion includes a second part of the locking ring comprising an annular ring around the circumference of the cap portion, the annular ring dimensioned and configured to matingly engage the annular groove on the body portion. In these exemplary embodiments, the annular ring on the cap portion has a depth and a width equal to or smaller than the annular groove on the body portion such that the annular ring of the cap portion freely nests inside the annular groove of the body portion when the cap portion is sealed on the body portion.

In some exemplary embodiments according to the invention, height of the annular ring of the cap portion is equal to or greater than the depth of the annular groove of the body portion. In some exemplary embodiments, the annular ring of the cap portion is between about 0.05 mm to 0.15 mm high and the annular groove of the body portion is between about 0.03 to 0.14 mm deep. In various other exemplary embodiments, the width of the annular groove of the body portion is between about 2.0 mm to about 6.0 mm and the width of the annular ring of the cap portion is between about 1.0 mm to about 5.0 mm. In other exemplary embodiments, according to the invention, the radius of the annular ring of the cap portion is 1.5 mm to 4 mm and the radius of the annular groove of the body portion 2 mm to 5 mm.

In various exemplary embodiments, the invention further includes a shoulder between the rounded top and the annular ring of the cap portion. In various exemplary embodiments, the length of shoulder of the cap portion is between 0.2 mm to 1.2 mm, and the inner diameter of cap straight shoulder area is same as the outer diameter of body shoulder area.

In other exemplary embodiments, the tapered rim of the body portion has a bevel angle of from about 4° to 10°. In various exemplary embodiments, the tapered rim of the body portion has a bevel length from 0.5 mm to 1.5 mm. In various embodiments, the cap thickness is from 0.09 mm to 0.2 mm. In other exemplary embodiments, the body portion has a thickness of from about 0.06 mm to about 0.15 mm.

In still other exemplary embodiments, includes round junctions connecting the annular groove of both body and cap portion and cylinder area of both cap and body, the straight shoulder area of both body and cap portion and the annular groove of both body and cap portion. In various exemplary embodiments, the radius of the round junction is between 0.1 mm to 1 mm.

In various other exemplary embodiments, the invention includes one or more dimples in the cap between the rim and the locking ring dimensioned and configured to matingly engage with the annular ring of the body portion and defining a half-locked position.

In still other exemplary embodiments, the invention includes a gelatin capsule for containing a hygroscopic material comprising:

(i) a body portion comprising an open top having a tapered rim, a shoulder area and a closed rounded bottom, and a first portion of a locking ring comprising an annular groove;

(ii) a cap portion comprising an a closed top, a shoulder area a second portion of a locking ring comprising an annular ring;

(iii) the locking ring further comprising the annular groove that is equal to or wider than the width of the annular ring and the annular ring that is equal to or higher than the depth of the annular groove.

In various exemplary embodiments, the annular ring of the cap portion is between about 0.05 mm to 0.15 mm high and the annular groove of the body portion is between about 0.03 to 0.14 mm deep.

In still other exemplary embodiments, wherein the width of the annular groove of the body portion is between about 2.0 mm to about 6.0 mm and the width of the annular ring of the cap portion is between about 1.0 mm to about 5.0 mm. In some exemplary embodiments, the radius of the annular ring of the cap portion is 1.5 mm to 4 mm and the radius of the annular groove of the body portion 2 mm to 5 mm. In still other embodiments the invention includes a shoulder between the rounded top and the annular ring of the cap portion. In various exemplary embodiments, the invention further includes the shoulder length of the cap portion is between 0.2 mm to 1.2 mm, and the inner diameter of cap straight shoulder area is same as the outer diameter of body shoulder area.

In still other exemplary embodiments, the invention includes one or more dimples in the cap between the rim and the locking ring dimensioned and configured to matingly engage with the annular ring of the body portion and defining a half-locked position.

In yet other exemplary embodiments the invention comprises a locking ring for a gelatin capsule. In these exemplary embodiments, the invention comprises a locking ring including an annular groove on a first portion of a gel capsule and an annular ring a second portion of a gel capsule. In this exemplary embodiment, the annular groove and the annular ring are designed and configured to matingly engage with a locking force of about 50 MPa to about 5 MPa. In various exemplary embodiments the locking force is between about 25 MPA to about MPa. In still other exemplary embodiments, the locking force results from a differential in the size diameter of the first portion of the gel capsule to the second portion of the gel capsule of about between 0.10% and 0.50%. In some exemplary embodiments the size difference is about 0.25%. In some exemplary embodiments, the locking force results from the annular ring on the second portion having a width equal to or smaller than the annular groove on the first portion such that the annular ring nests inside the annular groove. In various exemplary embodiments, the height of the annular ring is the equal to or greater than the depth of the annular groove.

These and other features and advantages of various exemplary embodiments of the methods according to this invention are described in, or are apparent from, the following detailed description of various exemplary embodiments of the methods according to this invention.

BRIEF DESCRIPTION OF THE FIGURES

Various exemplary embodiments of the compositions and methods according to the invention will be described in detail, with reference to the following figures wherein.

DETAILED DESCRIPTION OF THE EXEMPLARY EMBODIMENTS

Figure 1:
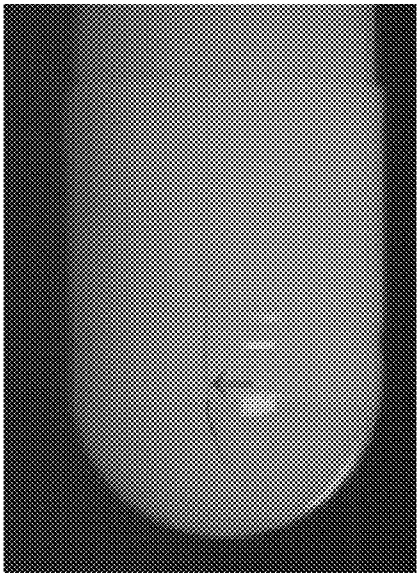
FIG. 1 is a photograph of a conventional gel-capsule, the arrow identifies cracking in the cap that spontaneously occurs after filling with hygroscopic materials.

The present invention is directed to a gelatin capsule that is designed to impart less tensile stress on the component parts when it is in the closed position and therefore experiences less spontaneous breakage particularly when filled with hygroscopic liquids. The gelatin capsule comprises a cap portion and a body portion. The cap portion includes an annular ring and the body portion includes an annular groove. Together, the annular ring and the annular groove comprise a locking ring. In one embodiment of the invention, the annular ring is narrower than the annular groove but the annular ring is higher than the depth of the annular groove. The body portion also includes a tapered ring configured such that, in the closed position, the rim of the body portion does not contact the cap portion.

Therefore, in various exemplary embodiments, the invention comprises a gelatin capsule comprising a body portion and a cap portion. In some embodiments the body portion has an open top including a tapered rim, shoulder area and a closed rounded bottom. In these embodiments, the cap portion having a closed rounded top, a shoulder area and open bottom, the top portion dimensioned and configured to fit over the body portion to comprise a closed capsule. In some exemplary embodiments, the tapered rim is dimensioned and configured such that when the cap is secured, the rim does not contact the cap portion. In some exemplary embodiments, the body portion further includes a first part of a locking ring comprising an annular groove around the circumference of the body portion. In these exemplary embodiments, the cap portion includes a second part of the locking ring comprising an annular ring around the circumference of the cap portion, the annular ring dimensioned and configured to matingly engage the annular groove on the body portion. In these exemplary embodiments, the annular ring on the cap portion has a depth and a width equal to or smaller than the annular groove on the body portion such that the annular ring of the cap portion freely nests inside the annular groove of the body portion when the cap portion is sealed on the body portion.

In some exemplary embodiments according to the invention, height of the annular ring of the cap portion is equal to or greater than the depth of the annular groove of the body portion. In some exemplary embodiments, the annular ring of the cap portion is between about 0.05 mm to 0.15 mm high and the annular groove of the body portion is between about 0.03 to 0.14 mm deep. In various other exemplary embodiments, the width of the annular groove of the body portion is between about 2.0 mm to about 6.0 mm and the width of the annular ring of the cap portion is between about 1.0 mm to about 5.0 mm. In some exemplary embodiments, according to the invention, the radius of the annular ring of the cap portion is 1.5 mm to 4 mm and the radius of the annular groove of the body portion 2 mm to 5 mm.

In various exemplary embodiments, the invention further includes a shoulder between the rounded top and the annular ring of the cap portion. In various exemplary embodiments, the length of shoulder of the cap portion is between 0.2 mm to 1.2 mm, and the inner diameter of cap straight shoulder area is same as the outer diameter of body shoulder area.

In other exemplary embodiments, the tapered rim of the body portion has a bevel angle of from about 4° to 10°. In various exemplary embodiments, the tapered rim of the body portion has a bevel length from 0.5 mm to 1.5 mm. In various embodiments, the cap thickness is from 0.09 mm to 0.2 mm. In other exemplary embodiments, the body portion has a thickness of from about 0.06 mm to about 0.15 mm.

In still other exemplary embodiments, includes round junctions connecting the annular groove of both body and cap portion and cylinder area of both cap and body, the straight shoulder area of both body and cap portion and the annular groove of both body and cap portion. In various exemplary embodiments, the radius of the round junction is between 0.1 mm to 1 mm.

In various other exemplary embodiments, the invention includes one or more dimples in the cap between the rim and the locking ring dimensioned and configured to matingly engage with the annular ring of the body portion and defining a half-locked position.

In still other exemplary embodiments, the invention includes a gelatin capsule for containing a hygroscopic material comprising:

(i) a body portion comprising an open top having a tapered rim, a shoulder area and a closed rounded bottom, and a first portion of a locking ring comprising an annular groove;

(ii) a cap portion comprising a closed top, a shoulder and a second portion of a locking ring comprising an annular ring;

(iii) the locking ring further comprising the annular groove that is equal to or wider than the width of the annular ring and the annular ring that is equal to or higher than the depth of the annular groove.

In various exemplary embodiments, the annular ring of the cap portion is between about 0.05 mm to 0.15 mm high and the annular groove of the body portion is between about 0.03 to 0.14 mm deep.

In still other exemplary embodiments, wherein the width of the annular groove of the body portion is between about 2.0 mm to about 6.0 mm and the width of the annular ring of the cap portion is between about 1.0 mm to about 5.0 mm. In some exemplary embodiments, the radius of the annular ring of the cap portion is 1.5 mm to 4 mm and the radius of the annular groove of the body portion 2 mm to 5 mm. In still other embodiments the invention includes a shoulder between the rounded top and the annular ring of the cap portion. In various exemplary embodiments, the invention further includes the shoulder length of the cap portion is between 0.2 mm to 1.2 mm, and the inner diameter of cap straight shoulder area is same as the outer diameter of body shoulder area.

In other exemplary embodiments, the invention includes one or more dimples in the cap between the rim and the locking ring dimensioned and configured to matingly engage with the annular ring of the body portion and defining a half-locked position.

In yet other exemplary embodiments the invention comprises a locking ring for a gelatin capsule. In these exemplary embodiments, the invention comprises a locking ring including an annular groove on a first portion of a gel capsule and an annular ring a second portion of a gel capsule. In this exemplary embodiment, the annular groove and the annular ring are designed and configured to matingly engage with a locking force of about 50 MPa to about 5 MPa. In various exemplary embodiments the locking force is between about 25 MPA to about 10 MPa. In still other exemplary embodiments, the locking force results from a differential in the size diameter of the first portion of the gel capsule to the second portion of the gel capsule of about between 0.10% and 0.50%. In some exemplary embodiments the size difference is about 0.25%. In some exemplary embodiments, the locking force results from the annular ring on the second portion having a width equal to or smaller than the annular groove on the first portion such that the annular ring nests inside the annular groove. In various exemplary embodiments, the height of the annular ring is the equal to or greater than the depth of the annular groove.

Methods of making gelatin capsules are well known in the art. See, for example, U.S. Pat. Nos. 525,844 and 525,845, hereby incorporated by reference in their entirety. Basically, the capsules are made in two parts by dipping metal rods in molten starch, cellulose solution or a solution of gelatin, water, and glycerin. The capsules are supplied as closed units to the pharmaceutical manufacturer. Before use, the two halves are separated, the capsule is filled. The capsules are then packaged and stored ready for shipment.

Upon investigation of the occurrence of spontaneous cracking of gel capsules, the inventors made four important observations from their initial analysis. First, capsules would spontaneously break after banding while drying on trays. This observation was important because it eliminated mechanical impact as a cause of capsule cracking. Second, the inventors noticed that breakage always occurred on the capsule cap (FIG. 1). This is linked to the dipping process used to make the empty capsules, which results in the shoulder area of the capsules becoming the thinnest and, therefore, the weakest area of the capsule. Furthermore, the shoulder area of the capsule cap coincides with the locking ring mechanism, where a tight interference fit between the body and cap is used to prevent the capsules from popping open after closure. This tight fit at the locking ring places additional stress at the thin shoulder area of the cap. Third, the inventors noticed that a significant number of capsules did not break at all. This observation was important because it indicates that there are capsule attributes that, if defined and controlled, could result in capsules that would be acceptable for use with hygroscopic fill materials. A fourth observation occurred some months later when the inventors attempted to repeat a study in which a large number of capsules broke when filled with polyethylene glycol (PEG) 400. However, when the study was repeated, the capsules did not break. The inventors then subsequently determined that the conflicting results stemmed from a difference in room humidity during manufacturing. It was found that the cracking rate of capsules filled with hygroscopic materials increased as humidity increased. This finding highlighted the importance of manufacturing conditions.

Following the observations made above, the inventors designed a variety of experiments to investigate the forces at work after capsule filling and to identify ways to limit or reduce spontaneous cracking. It is well established that water serves as a potent plasticizer in gelatin and that removing water results in a brittle capsule. Brittle materials have less ability to deform before fracturing. When a brittle capsule is cracked by an impact test, it is because the capsule shell wall deflects more than its ability to deform. Coupled with this is the force needed to cause the deflection. A brittle but strong capsule will require more force to deflect the shell wall enough that it cracks. Less brittle capsule shells can deflect more before cracking. Therefore, brittleness alone is not enough to cause a capsule to break. An additional force strong enough to deflect the capsule shell wall beyond its elongation limits is required. Brittleness simply decreases the deflection distance required for a fracture to occur. So the model for impact induced cracking is fairly straightforward; however, the inventors wanted to know what caused the capsules to crack spontaneously when exposed to hygroscopic materials and no external forces impinged on the capsule. Therefore, the inventors designed and undertook a series of experiments to understand this problem and identify solutions.

Various exemplary embodiments of devices and compounds as generally described above and methods according to this invention will be understood more readily by reference to the following examples, which are provided by way of illustration and are not intended to be limiting of the invention in any fashion.

Example 1

Hygroscopic Fills and Shoulder Thickness

Figure 2:
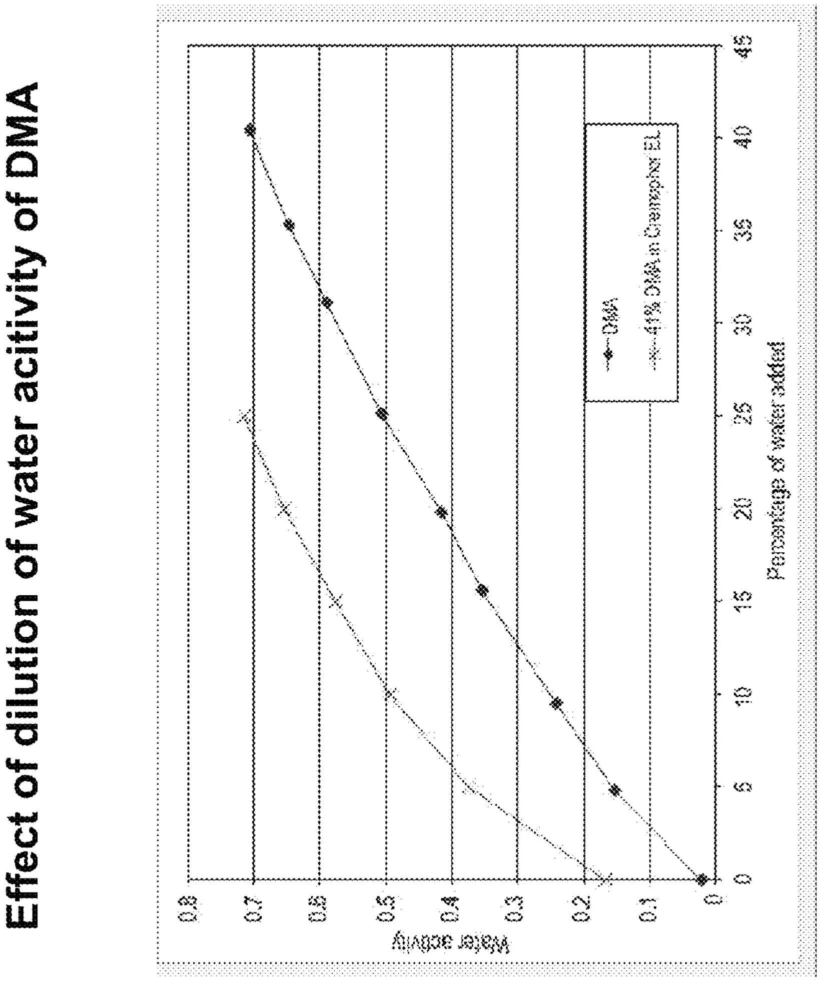
FIG. 2 is a plot of the effect of water activity on a model hygroscopic solvent.

To study this problem, of spontaneous breakage and hygroscopic fills the inventors initially used PEG 400, but those experiments required fairly large batches to generate significant numbers of cracked capsules. Therefore, dimethylacetamide (DMA), a solvent that is more hygroscopic compared to typical solvent systems used in formulation applications was used instead. Pure DMA will cause most capsules to crack, often within seconds. Diluting DMA with a less hygroscopic solvent reduces its hygroscopicity and allows a finer resolution of capsule failure rates. The degree of hygroscopicity can be readily adjusted by varying the ratio of DMA with a less hygroscopic solvent. FIG. 2 depicts water activity curves for DMA and DMA diluted with Cremophor EL, a polyethoxylated castor oil manufactured by BASF, Florham Park, N.J. The higher the water activity, the higher the amount of free water molecules, and thus the lower the hygroscopicity. By increasing the amount of DMA, water activity decreases. This results in greater hygroscopicity and less capsule shell plasticity, which increases the shell's propensity to crack. For most of the studies 41 percent DMA in Cremophor EL was used in order to discriminate between different capsules and conditions within a reasonable timeframe.

Figure 3:
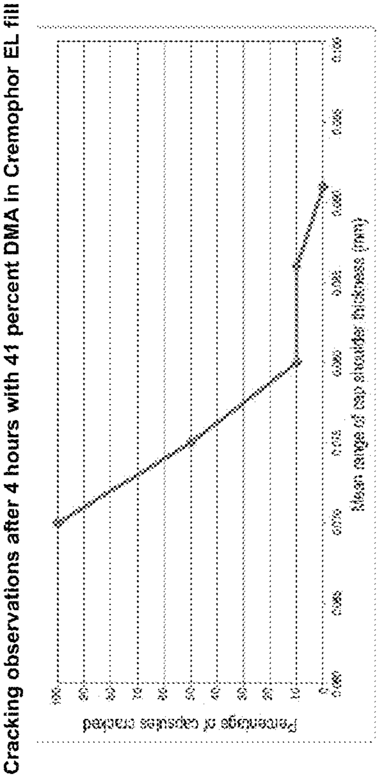
FIG. 3 is a plot of the spontaneous cracking observed in after 4 hours with 41 percent DMA in Cremophor® EL fill.

Using these DMA systems allowed the inventors to make relative comparisons between capsules to evaluate various parameters. One area of focus was shoulder thickness and its contribution to cracking. Since the shoulder area of the capsule tends to be the thinnest area, as well as the point of failure, capsules with varying shoulder thicknesses were compared. FIG. 3 shows the percentage of capsules that cracked after 4 hours of exposure to a 41 percent DMA solution relative to shoulder thickness from a lot of capsules that had been sorted into shoulder thickness ranges. A higher incidence of cracking was observed when the capsules had thinner shoulders compared to capsules with thicker shoulders. The graph shows an inflection point around 0.080 millimeter, which appears to indicate a point of diminishing returns with respect to shoulder thickness. It should be noted that these data are relevant to the particular concentration of DMA used. Higher concentrations of DMA will increase the proportion of capsules breaking, and lower concentrations will decrease the breakage rate for a given shoulder thickness. The critical thickness at which breakage drops off will depend on the actual solvent used; however, the method used allowed the inventors to readily make relative comparisons between different lots of capsules.

Example 2

Water Content and Differing Stresses

Figure 4:
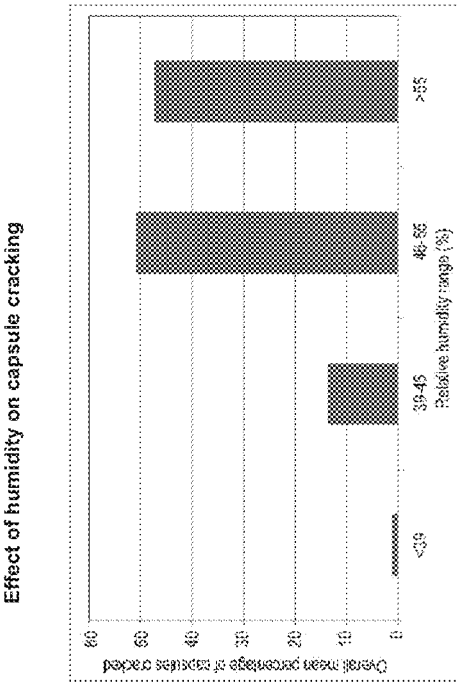
FIG. 4 is a graph illustrating the effect of humidity on capsule cracking.

The inventors also investigated the impact of capsule water content on cracking, which entailed storing the capsules at various relative humidities (RHs) and then drying them to less than 1 percent water concentration in a desiccator or oven. Using DMA testing, the inventors found a correlation of increased capsule cracking with increasing capsule water content. FIG. 4 shows data compiled after a study in which 41 percent DMA was used on capsules with a wide range of shoulder thicknesses. The graph provides a comparison of cracking levels at an RH typical of most manufacturing environments. Capsules dried to lower water content tolerated higher concentrations of DMA before cracking compared to capsules with higher water content. This data identified a situation that counters traditional theory: The drier capsules (more brittle) were less likely to spontaneously crack than the less brittle capsules with higher water content.

One explanation for this behavior would be the presence of some internal factor or factors that were applying enough stress to the capsule to exceed the elongation capability of the gelatin. The inventors speculated that dimensional changes in the gelatin itself might be responsible for the stress and thus, for the cracking. To test this hypothesis, DMA was applied to one side of a thin strip of gelatin and observed that this caused the gelatin strip to curl toward the DMA side of the strip. This indicated that DMA caused the gelatin surface to shrink where it was applied. The dimensional changes in gelatin films after drying them or exposing them to DMA was then measured. It was found that the gelatin films shrank approximately 2.6 percent when dried from 30 percent RH to near 0 percent RH.

Figure 5:
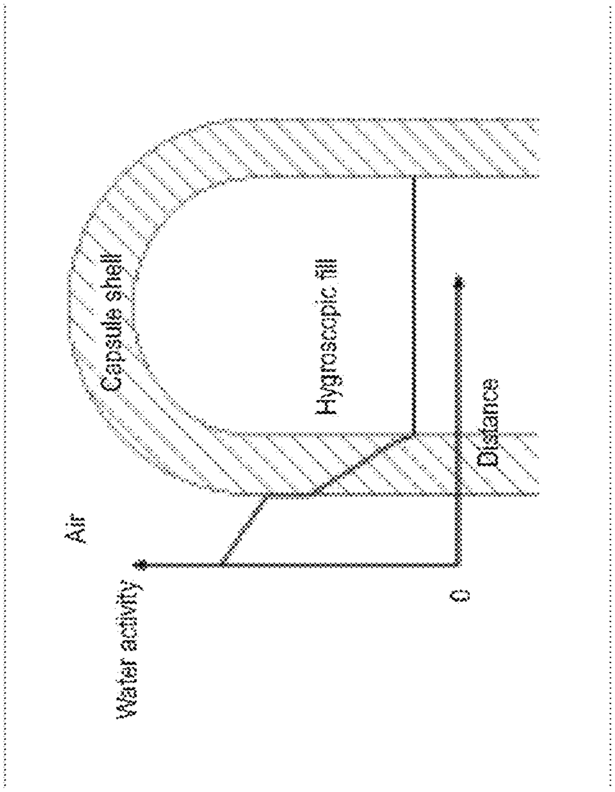
FIG. 5 is a schematic diagram illustrating the moisture gradient across capsule shell wall when filled with hygroscopic material.
Figure 6:
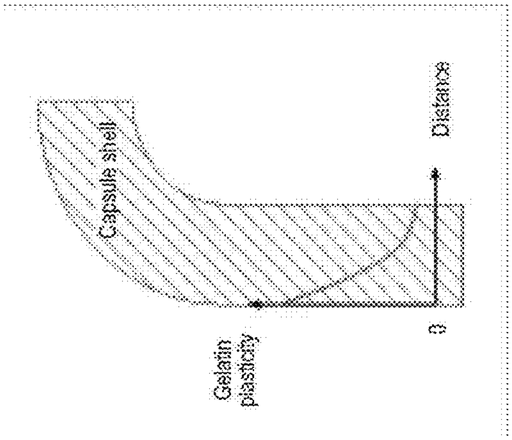
FIG. 6 is a schematic diagram illustrating the gelatin plasticity gradient across capsule shell wall when filled with hygroscopic material.
Figure 7:
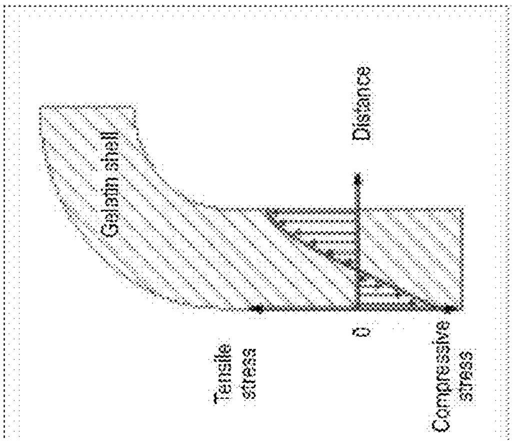
FIG. 7 is a schematic diagram illustrating the stress distribution across capsule shell wall when filled with hygroscopic material.

Based on these observations, the inventors hypothesized that a cascade of events occurs that explains spontaneous capsule cracking. First, when a capsule is filled with hygroscopic material, water is pulled from the inside surface of the shell, creating a diffused moisture gradient from inside to outside (FIG. 5). Second, as moisture is removed, a plasticity gradient corresponding to the moisture gradient develops, and the inner layer of the gelatin shell becomes brittle, which means that its ability to elongate before failure decreases (FIG. 6). Third, as the gelatin begins to shrink, the inner layer of the capsule tends to shrink more than the outer layer because the DMA causes faster water removal at the inside layer, creating a moisture gradient. This places the inside layer of the capsule shell under tension, while the outside layer is under compression (FIG. 7). The dome shaped capsule ends constrain the gelatin shrinkage more than the body area does. With the added interaction between cap and body, especially at the locking mechanism, the cap end will sustain more tensile stress than the body end. So the capsule enters a state that, if the tension force due to the gelatin shrinkage exceeds the elongation ability of the gelatin (reduced because the gelatin lost water and is now more brittle), the shell will split or crack to relieve the tension forces. Combined with the weakness of the shoulder area of the capsule and the additional stress of the interference fit of the body at the cap, the resulting failure point occurs in this area.

The moisture gradient across the shell wall is important to the occurrence of spontaneous capsule cracking. The ratio of tension to compression between the inside and outside walls increases the more hygroscopic the fill is and the more water the shell contains. In the studies described herein, when capsules were dried to negligible water content, they could withstand higher DMA exposure because the moisture gradient across the capsule wall was also negligible. This hypothesis explains why the spontaneous cracking rate decreased at lower-humidity manufacturing conditions: Shell water content is proportional to the RH.

While, the DMA solvent used in these studies is significantly more hygroscopic than the materials that would typically be used in pharmaceutical applications, such as PEG 400, it allowed the inventors to determine critical parameters associated with capsule breakage, as opposed to a QC method of monitoring capsule quality. However, the inventors have successfully used this method to screen capsules in order to choose the most robust lot when a potential exists for capsule breakage.

Example 3

Characterization of Stress Placed on Capsule Wall

Figure 8C:
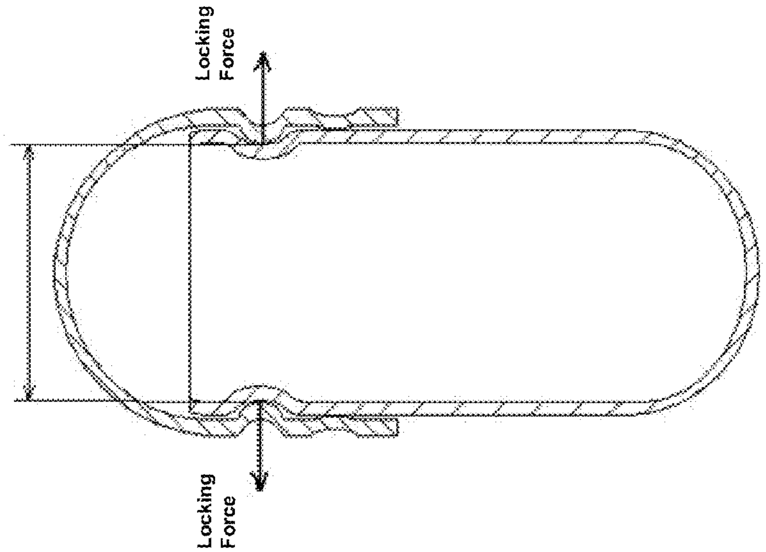
FIGS. 8A, 8B and 8C are schematic diagrams illustrating the tensile stress exerted on a conventional capsule components during use.
Figure 8B:
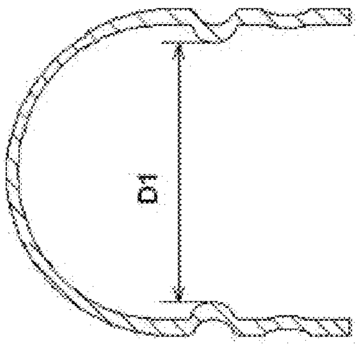
Figure 8A:
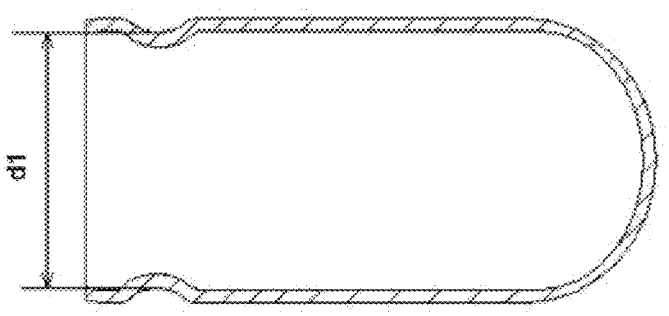

Following the assumptions identified in the preceding investigations, the inventors developed a model of the stress exerted on the capsule following filling and closure, this is illustrated in FIGS. 8A, B and C. When cap and body are separated, the cap locking ring inner diameter is D1, and the body locking ring outer diameter is d1. Usually d1 is bigger than D1. Conventional wisdom reasons that by making d1 greater than D1, the locking force will be greater with less chance of leakage of the contents. After fully closed, the cap locking ring apex contacts the body locking ring. The cap expands a little bit and the body shrinks a little bit at the locking ring area to make the body and cap fit into each other. The cap and body locking ring diameter now becomes D2. The size sequence here is: d1>D2>D1. Since in most capsule designs, d1 is bigger than D1, then after closing, D2 is bigger than D1 due to the cap expansion. This expansion is the reason for cap locking force. This force is perpendicular to the capsule axis. During the investigations resulting in the instant invention, it was found this radial locking force is a main reason for capsule cracking.

Example 4

Identification of Stress Raisers

By identifying the forces exerted on the gel capsule parts and the stresses imparted thereby the inventors' goal was to: 1) erase all the pre-existing force between cap and body after closing; and 2) erase stress raisers in capsule design. (A stress raiser is an improper geometry design to cause local stress concentration. The stress in this area is well above the average stress level in the whole product. For example, airplane windows always have round corners. Because a sharp corner is a stress raiser, stress at the corner area is much higher than other areas. Cracks develop at corner areas after a sufficient period of flying.). The following characteristics were identified as being important stress raisers:

Same cap locking ring inner diameter D1 and body locking ring outer diameter d1. This is to erase the pre-existing force.

Figure 11:
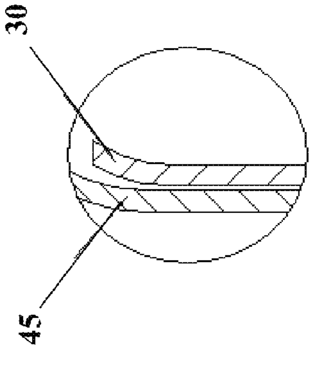
FIG. 11 is a blown-up cross-sectional representation of the area '1' identified in FIG. 9 illustrating the relationship between the rim of the body portion and the shoulder of the cap portion in this exemplary embodiment of the invention.

Avoid contact force between body rim and cap dome after closing (FIG. 11). Body rim 30 should stop just before touching the cap dome 70. This is to erase the pre-existing force. Conventional capsules have a high contact force to seal capsules.

Figure 12:
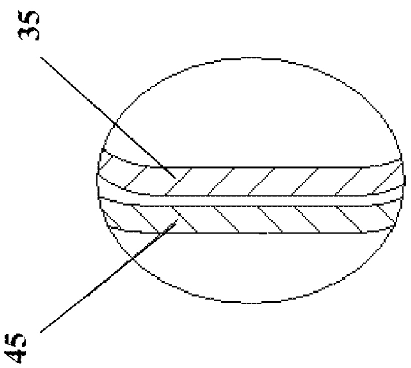
FIG. 12 is a blow up cross-sectional representation of the area '2' identified in FIG. 9 illustrating the relationship between the shoulders of the cap portion and the body portion in this exemplary embodiment of the invention.

Short straight shoulder is to avoid stress raiser (FIG. 12).

No contact force between cap and body straight shoulder is to erase the pre-existing force.

A round "corner" R1 (FIG. 13) at the junctures of the annular ring with the body 15 and the annular groove 50 with the cap is to avoid stress raisers.

A relatively big and close R2, R3 (FIG. 13) is to gain a bigger cap body locking ring contact area. This is to avoid stress raisers. This is in contrast to commercially available gel capsules which have a small contact area and a body locking ring that is easy to crack.

Further, the body rim has a tapered edge. This will make the body slide into the cap easily and smoothly. This is to make capsule closing easy and avoid capsule damage during closing.

High H2, H1 is to prevent cap body separation.

The prelocking brings prelocking force to make sure cap and body stay together during transportation before filling.

High cap thickness. Currently most capsule cap shoulder area thickness is about 0.07~0.09 mm. If this thickness rises to 0.15 mm, the risk of capsule breakage should decrease.

Example 5

Design of Break Resistant Capsule

Due to the identification of the stress exerted on the capsule wall discussed above and illustrated in FIGS. 8A, B and C, the inventors found that to avoid this locking force in liquid fill capsules, in this new design, it was identified that d1 should be the same as D1. So after closing, d1=D2=D1. This was found to be an important factor in capsule design that resists spontaneous breaking. The inventors research identified that this radial locking force is one of the main reasons for capsule cracking.

Figure 9:
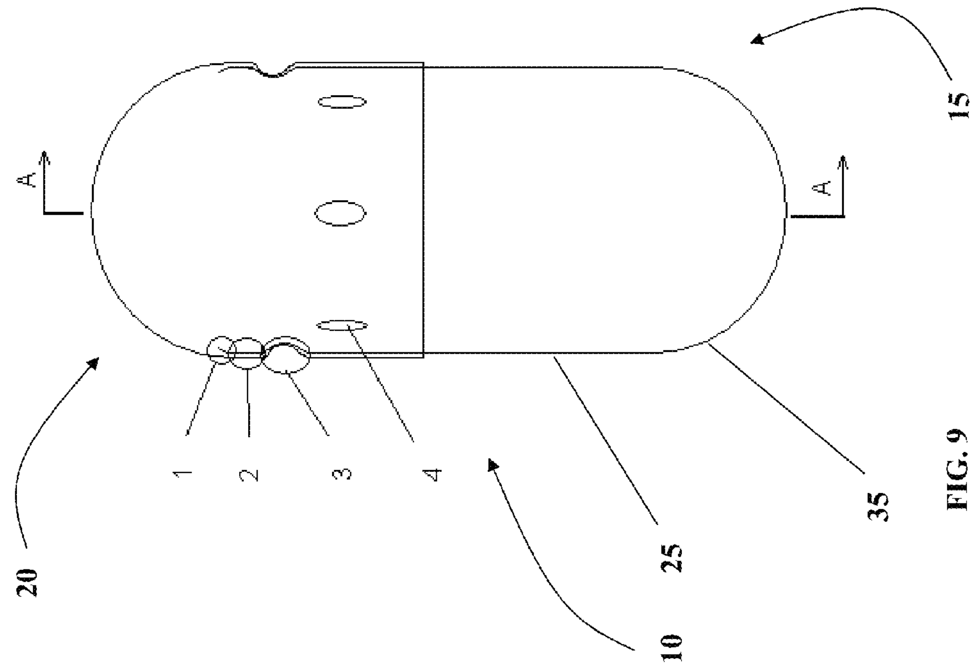
FIG. 9 is a diagrammatic representation of one exemplary embodiment of a gel capsule according to the invention.

Therefore, in order to overcome the problems of spontaneous cracking in conventional gel capsules, the inventors provide herein an improved gel cap that minimizes the problems of spontaneous breakage seen in conventional gel capsules. FIG. 9 shows one exemplary embodiment of a gelatin capsule 10 according to the invention. As shown, the gel capsule 10 includes a body portion 15 and a cap portion 20. The body portion 15 includes a shoulder 25 having a tapered rim 30 and a closed round bottom 35. In addition, the body portion 15 includes an annular groove 50 thereupon which is distal to the rim 30. The cap portion 20 includes a rounded top 70, an open rim 75 and a short shoulder 45 proximate to the rounded top that is followed by an annular ring and followed by a plurality of dimples 65 in the cap which form protrusions on the inner surface of the cap 20.

Figure 10:
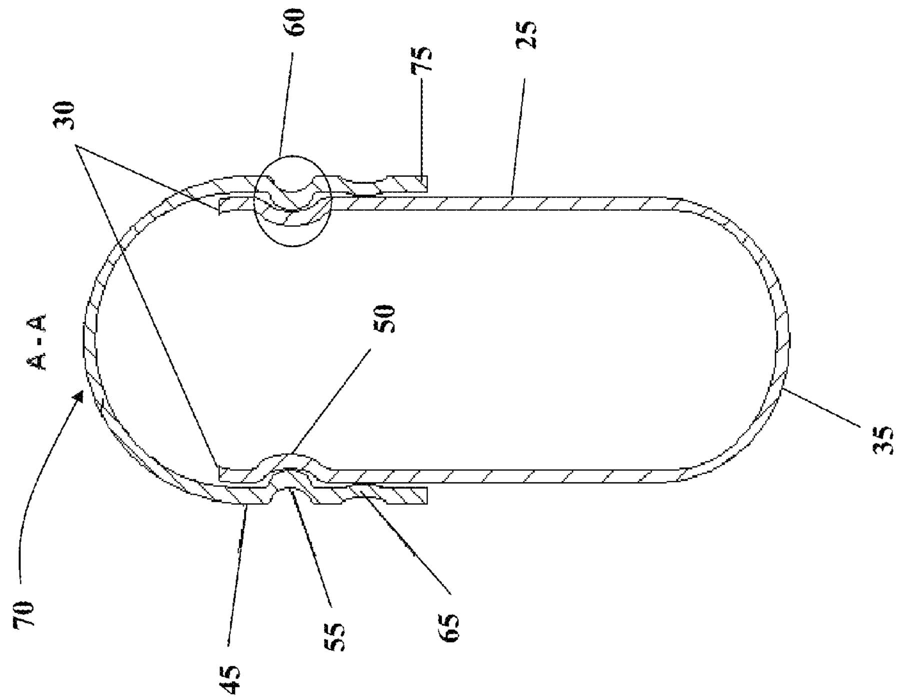
FIG. 10 is a cross section of the exemplary embodiment of the invention illustrated in FIG. 9 taken along the plane 'A'.

FIG. 10 is a cross section of the exemplary embodiment of gelatin capsule according to the invention taken along plane A-A. As illustrated, the body portion 15 terminates in a tapered rim 30 which does not contact the interior shoulder 45 of the cap 20. Also shown is the annular groove 50 of the body portion 15 which together with the annular ring 55 of the cap portion 20 comprises a locking ring 60 keeping the cap portion 20 and the body portion 15 in the locked position. Also shown are dimples 65 spaced in an annular path around the bottom portion of the cap between the annular ring 55 and the cap rim 75. The dimples are aligned to engage with the annular groove 50 in a non-locking fashion so as to pair a cap portion 20 and a body portion 15 during shipment but allow the two parts to be separated for loading.

FIG. 11 is an exploded view of the region labeled '1' in FIG. 9 and illustrates the position of the tapered rim 30 of the body portion 15 and the shoulder 45 of the cap portion 20, showing that there is no contact with the capsule in the closed position. In addition, the tapered rim 30 allows an easier fit of the body portion 15 into the cap portion 20 for closing.

FIG. 12 is an exploded view of the area '2' shown in FIG. 9. This view shows the relationship of the cap 20 and body portions. In the exemplary embodiment shown the length of the cap shoulder is about between 0.5 to 0.8 mm. This length moves the annular ring down compared with conventional gel capsules and provides a more uniform thickness accordingly. The size difference between the cap portion 20 and the body portion in this area should be close to zero to avoid any contacting force.

Figure 13:
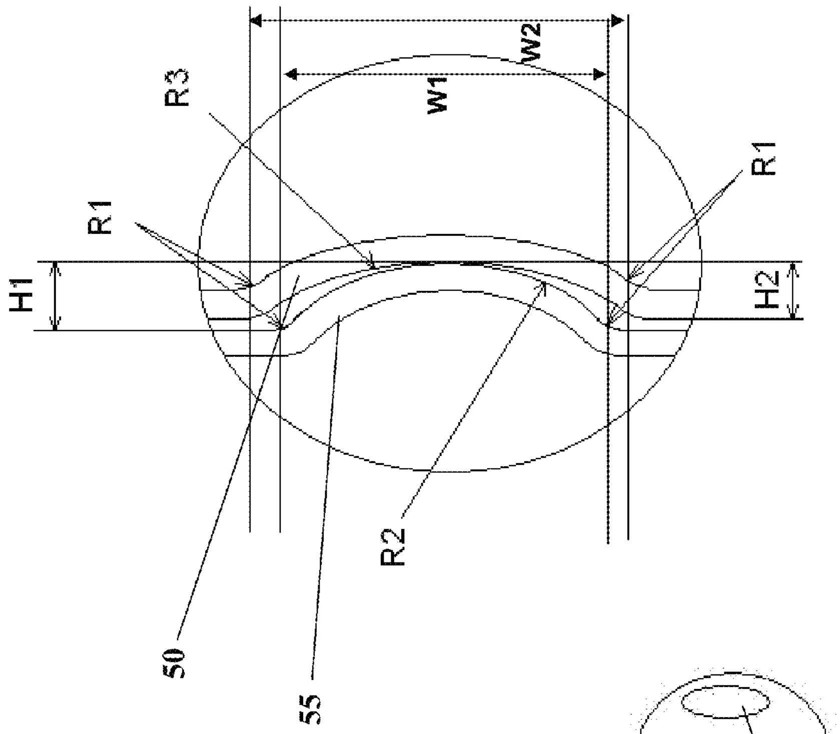
FIG. 13 is a blown-up cross sectional representation of one exemplary embodiment of the locking-ring illustrated in area '3' shown in FIG. 9.

FIG. 13 is an exploded view of the area identified as '3' in FIG. 9, which comprises the locking ring 60 comprised of the annular ring 55 and the annular groove 50. In this exemplary embodiment, H1 represent the height of the annular ring while H2 represent the depth of the annular groove. As illustrated the annular ring has a greater height than the depth of the annular groove. This difference in size allows the ring 55 to lock firmly into the cap without deforming the cap. In contrast, the radius of the annular ring R2 is smaller than the radius of the annular groove R3. The result is that the width of the locking ring W1 is less than the width W2 of the locking groove further limiting the stress applied to the cap upon drying. However, if W2 is much great than W1 the stress distribution will not be evenly distributed. Further, R1 illustrates that in various exemplary embodiments the junction of the annular ring 55 with the body 15 and the annular groove 50 with the cap 20 is rounded instead of squared off as is the norm with conventional gel capsules, this further limits the stress exerted on the cap portion 20 by the locking ring 60. Without being held to any particular theory, this may be the result of the stress exerted by the locking ring being more evenly distributed along the radial juncture as compared to squared junctions.

Figure 14:
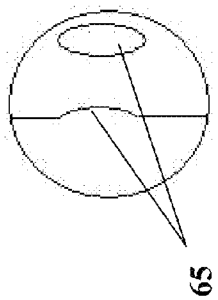
FIG. 14 is a blown-up view of the area identified as '4' in the exemplary embodiment of the invention illustrated in FIG. 10.

FIG. 14 is an exploded view of the area labeled 4 in FIG. 9. As shown dimples 65 are placed annularly around the cap portion between the rim 75 and the annular groove 50 to provide a non-locking position for the cap for shipping.

Those of skill in the art will appreciate that to keep cap and body in a locked state and prevent the cap from popping open, locking is necessary. To separate the cap and body from a fully locked state, force parallel to capsule axis is required. This force is to conquer the barrier of body locking ring height H2. When a force is applied parallel to capsule axis to try to separate cap and body, the bevel of the body locking ring tends to push the cap locking ring back. This prevents cap and body separation. This force is proportional to the body locking ring height H2. With a higher H2-*a* higher barrier, the cap body separation force will be higher. That means the chance to pop open will be lower. Now all the capsules are designed to have a high pre-existing locking force in the fully locked state. This high pre-existing locking force will also contribute to cap body separation force. That means a high pre-existing force in the fully locked state will make the cap and body more difficult to separate. But this high pre-existing locking force is not necessary if H2 is high.

Example 6

Optimization of Gel Capsule Locking Ring

As previously discussed, conventional manufacturing techniques teach that a high locking force is necessary to keep the capsule from leaking. However, the inventors' current research has identified that, surprisingly, the currently used high locking force is much greater than required to keep the capsule locked. The inventors' current research indicates that such high locking force is not required and, in fact, is detrimental as the excessive locking force is responsible for spontaneous breakage. Rather, what is necessary is good contact between the cap and body in the locking ring area. If capsules get sealed soon after closing the chance for leaking will be very low.

Therefore, while stresses and changes to traditional gel capsules design were disclosed in EXAMPLES 3-5, the data provided in EXAMPLE 2, which measured the force necessary to crack a thin gelatin strip resulted in the realization that, for conventional gel capsules, the locking force could be sufficiently decreased and still maintain the capsule cap locked position. This force was found to be around about 50 MPa to around about 5 MPa before the locking force resulted in breakage.

Further, this finding identified that a sufficient reduction in locking force could be achieved by reducing diameter of the capsule body in relation to the capsule cap by about 0.50%. However, the reduction in size may be as low as 0.10%. Therefore, for a 00 size capsule, the diameter difference should be from between about 0.04 to about 0.008. Of course, those of skill in the art will recognized that such a relative change in the diameter of the capsule portions can be achieved by increasing the size of a tradition gelatin capsule cap or decreasing the size of the body portion.

Example 7

Design Aspects of Capsules that Contribute to Spontaneous Cracking

Figure 15:
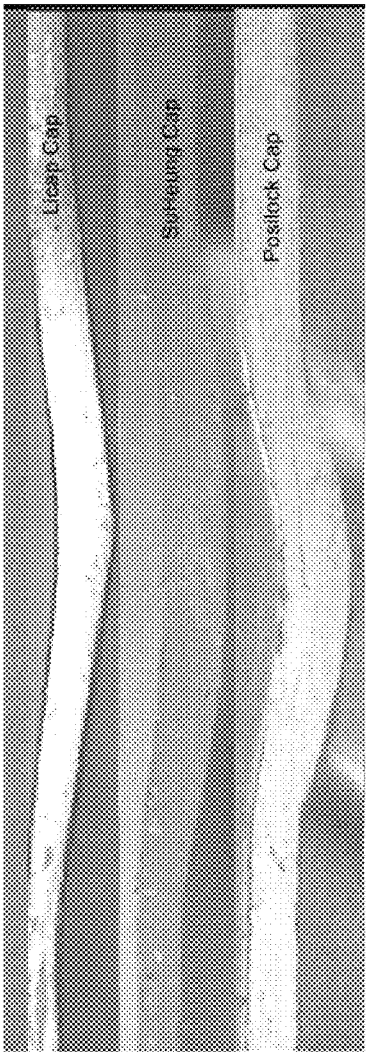
FIG. 15 is a comparison of cross sections of selected commercially available cap locking rings.
Figure 16:
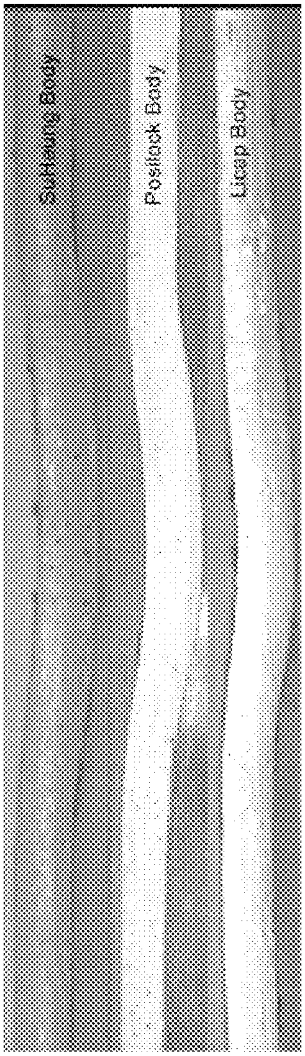
FIG. 16 is a comparison of cross sections of selected commercially available body locking rings.

The following experiments were performed on commercially available Capsugel LICAPS®, Qualicaps POSILOK®, and conventional SuHeung EMBO® capsules (not SuHeung liquid fill capsule design). Capsules from each of the three vendors were longitudinally cross sectioned and viewed under magnification and are presented in FIGS. 15 and 16. From these views a number of design features can be viewed and measured.

Starting with the locking ring, POSILOK® and SuHeung capsules both utilize an arc type locking ring design. The radius for the SuHeung capsules is substantially larger compared to POSILOK®. POSILOK® also exhibits a more abrupt transition that results in a stress raiser between the locking ring and the cap cylinder. LICAPS® utilizes an angular locking ring profile. The angular characteristics are well defined on the cap, but the body sometimes appears to be more arc type design.

Figure 17:
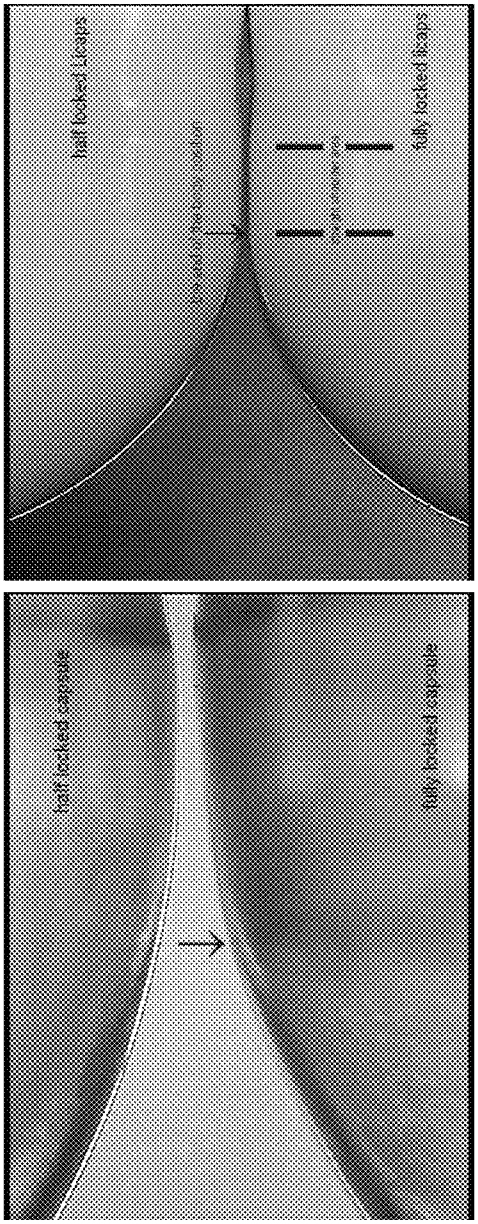
FIG. 17 is a magnified view illustrating Qualicaps size 00 on left. The arrow points to a small bump on the fully locked cap shoulder area caused by body-cap contact. This bump is not seen on the top pre-locked capsule. No bump is observed on LICAPS® due to straight section on shoulder area.

Body-rim/cap-shoulder interactions occur when the rim of the body is forced into the curvature of the cap. This is particularly prevalent on the POSILOK® capsule as can be seen in FIG. 17. It is lesser with respect to SuHeung, and essentially non-existent in LICAPS® which includes a straight segment on the cap after the locking ring to accommodate the body. As shown in the figure, the arrow points to a small bump on the fully locked cap shoulder area caused by body-cap contact. This bump is not seen on the top pre-locked capsule. No bump is observed on LICAPS® due to the straight section on the shoulder area.

Figure 18:
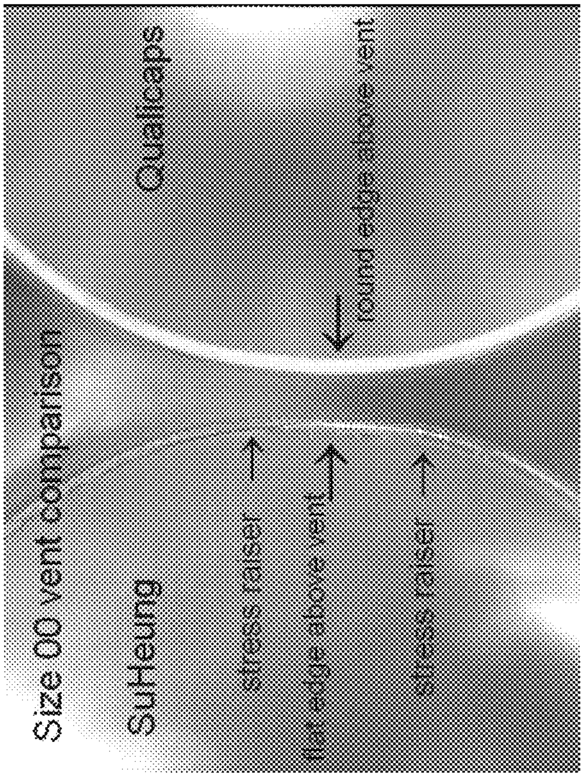
FIG. 18 is an end view of body venting structures.

Both SuHeung and POSILOK® incorporate body vents while LICAPS® is unvented (FIG. 18). An end view shows that SuHeung exhibits small corners where the vents transition into the body while Qualicaps POSILOK® does not.

Figure 19:
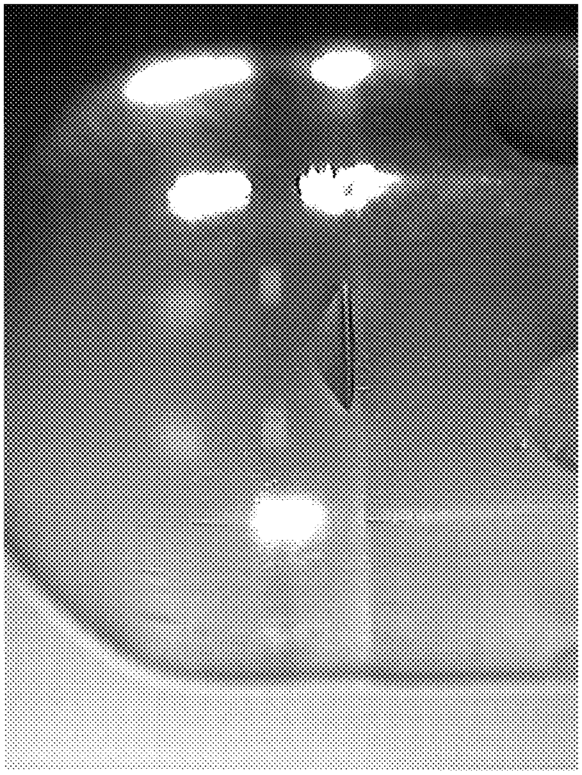
FIG. 19 is a magnified view of the EMBO® on the SuHeung capsule.

Finally the EMBO® feature on SuHeung is a small bump embossed into the cap near the locking ring (FIG. 19). This design is present to prevent both premature locking as well as popping open after closing.

TABLE 1

Capsule Locking Ring Features and Stress Raisers.

| Capsule | Cap Locking Ring | Body Locking Ring | Locking Ring Force | Body Rim/Cap-Shoulder Interaction | Other Stress Raisers |
|---|---|---|---|---|---|
| LICAPS ® | Angular (163°) | Arc (2.2 mm) | High | None | |
| POSILOK ® | Arc (2.17 mm) | Arc (0.90 mm) | High | High | Locking Ring Transition |
| SuHeung | Arc (2.33 mm) | Arc (3.47 mm) | Low | Moderate | EMBO ®, Body Vent |

A capsule may melt or dissolve when exposed to certain fill formulations, and this would represent a form of incompatibility directly related to the interaction of the fill formulation with the shell. The tendency of a capsule to spontaneously crack when exposed to a fill formulation may represent a form of interaction between the fill and the shell; however, it also is tied to mechanical stress on the shell. The common stresses seen can be broken into either tensile or compression stress. Compression stress is generally a force that is squeezing things together while tensile stress is a force that tends to pull things apart. Of the two stresses, tensile stress is the most critical to creating cracks in capsules. From the inventors' analysis, it was possible to define three origins of tensile stress inside the capsule shell. In reality, it is often the sum of these three origins that cause capsules to spontaneously crack.

The first one is the locking force exerted on the capsule after fully closing. Locking force is the force at the locking ring area between the cap and body to prevent cap and body separation after fully closing.

The second origin is the interaction between the body rim and the cap shoulder. This is the force that occurs when the end of the body presses against the dome of the cap.

The third origin is the shrinkage difference from the capsule shell inside layer and the outside layer if a hygroscopic fill is present that can draw water from the gelatin. This shrinkage difference causes tensile stress on the inside wall of the capsule and a compression stress on the outside wall of the capsule.

Besides tensile stress, the presence of stress raisers can lower the threshold necessary for a crack to occur. A stress raiser is a location in an object where stress is concentrated. Stress within a stress raiser is higher than the material average stress. When a concentrated stress exceeds the material's theoretical cohesive strength, a material can fail via a propagating crack. The real fracture strength of a material is always lower than the theoretical value because most materials contain stress raisers that concentrate stress.

Stress raisers can be a sharp angle of a transition zone, or a preformed hole or crack, or just an interface between two different materials. A good example of a stress raiser is the nearly invisible scratch used by glass cutters to create a stress point when cutting glass. Stress raisers are taken very seriously in mechanical design since they can reduce the ultimate strength of a mechanical design or significantly reduce the fatigue life of a design. In all the capsule designs evaluated, the inventors found design features that are stress raisers and were characterized by capsule cracking around these areas.

Although the inventors have identified these three types of stresses and the structure related stress raisers, it is still hard for us to know the real stress distribution at each specific location in a capsule. The real stress calculation is very complicated because of the irregular force distribution, irregular structure, boundary conditions, etc. Analysis using Finite Element Analysis (FEA) software can do this type of calculation. Predictions were based on the basic principles of fracture mechanics.

Figure 20:
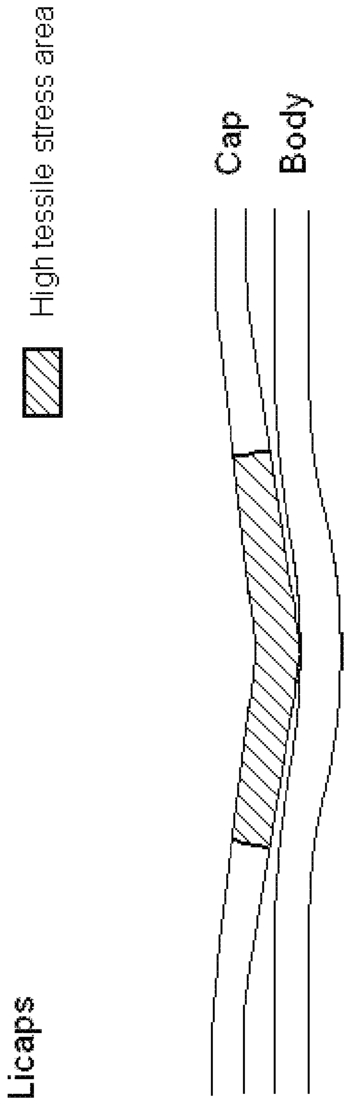
FIG. 20 is a schematic illustrating the LICAPS® locking ring.

If a more careful examination was made at stress zones and stress raisers in these designs, predictions as to the area of failure can be made. FIG. 20 shows the stress zone for LICAPS®, locking ring. The angular design of the cap locking ring creates a high tensile stress zone close to the apex of the angle, and therefore is predictive of cracking to initiate close to the apex of the locking ring groove.

Figure 21:
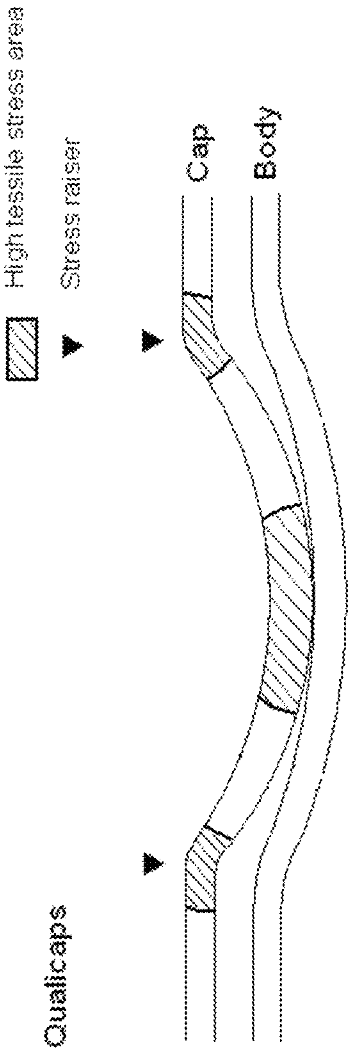
FIG. 21 a schematic illustrating the stress zones on the locking ring profile for Qualicaps POSILOK® capsules. In addition to the stress zone at the contact point of the cap with body, there are stress raisers where the locking ring transitions into the cylinder area of the cap. These abrupt transitions are particularly vulnerable to failure, and are predictive that these would be one of the primary failure areas.

FIG. 21 shows the stress zones on the locking ring profile for Qualicaps POSILOK® capsules. In addition to the stress zone at the contact point of the cap with body, there are stress raisers where the locking ring transitions into the cylinder area of the cap. These abrupt transitions are particularly vulnerable to failure, and one would predict that these would be one of the primary failure areas.

Figure 22:
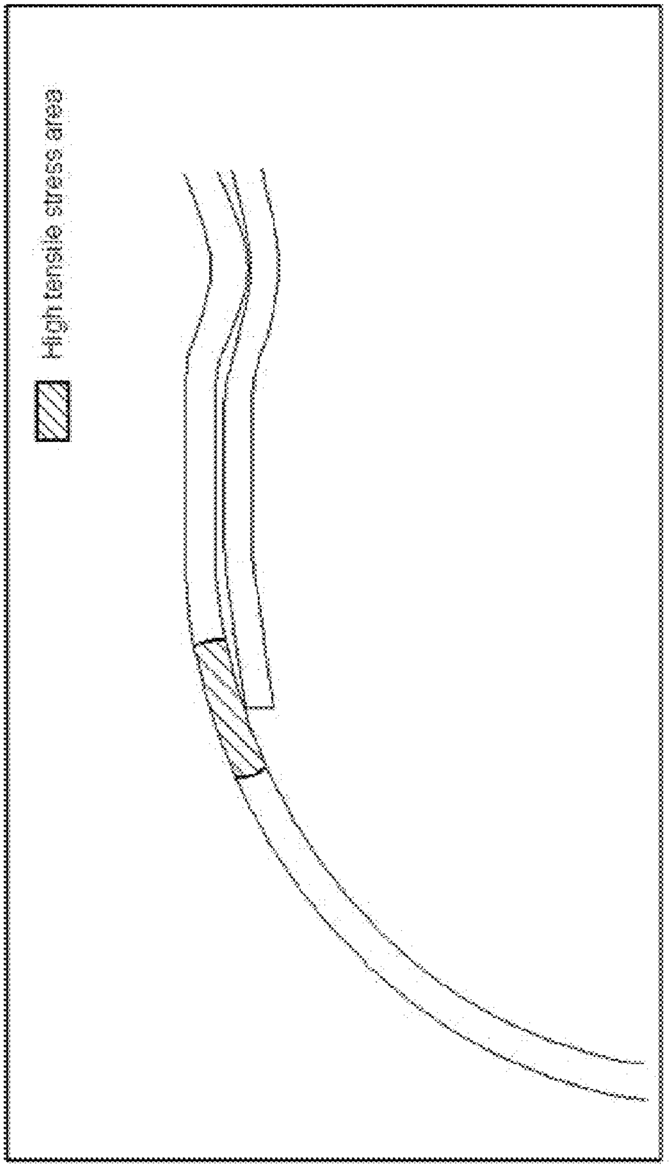
FIG. 22 is a schematic illustrating the body-rim/cap-shoulder interactions for the POSILOK® caps.

In addition, the body-rim/cap-shoulder interactions for the POSILOK® capsules (FIG. 22) result in high tensile stress on the cap shoulder area. This is particularly bad as the cap-shoulder also tends to be one of the weaker areas of the capsule.

Figure 23:
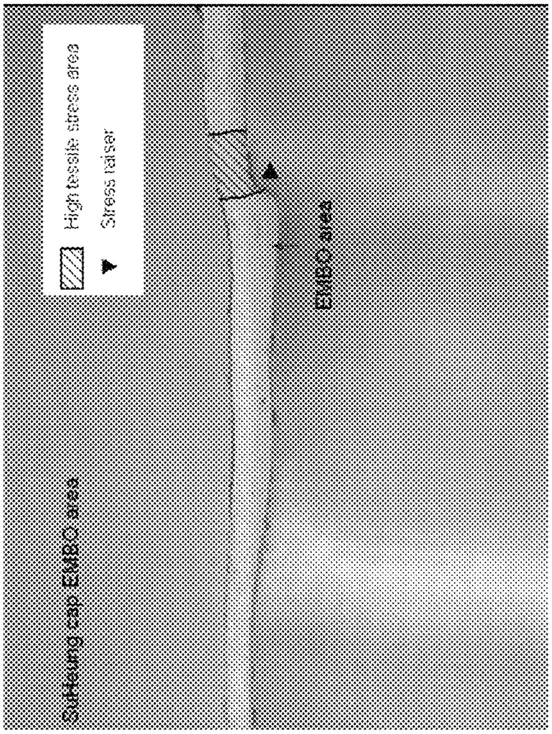
FIG. 23 is a cross section of EMBO® showing stress zone and stress raiser.

SuHeung capsules have relatively low locking force, so the tensile stress in general is low; however, the abrupt transitions of the EMBO® design create a stress raiser that increases vulnerability to failures (FIG. 23).

The inventors studied capsules by filling with DMA, PEG 200 or PEG 400. DMA represents a very aggressive hygroscopic fill material and can cause capsules to crack sometimes in a manner of seconds. Compared to DMA, PEGs are relatively mild. PEG 400 is weaker than PEG 200. In some cases, the inventors diluted pure DMA with Cremophor EL to adjust capsule cracking rate and provide better resolution of the cracking process. For PEGs or diluted DMA, it takes several hours or several days to crack a capsule, depending on the capsule condition and the relative humidity in the environment.

DMA Fill Test

Capsules were hand filled with a test solution, closed, and stored on a capsule stand. The filled capsules were observed periodically to monitor cracking. Tests showed that 50%~100% of both Qualicaps and LICAPS® will crack within several minutes to hours with pure DMA filling. Cracking rate is affected by the environmental conditions as well. At high relative humidity (RH), capsules crack quickly and the cracking rate is high.

Figure 24:
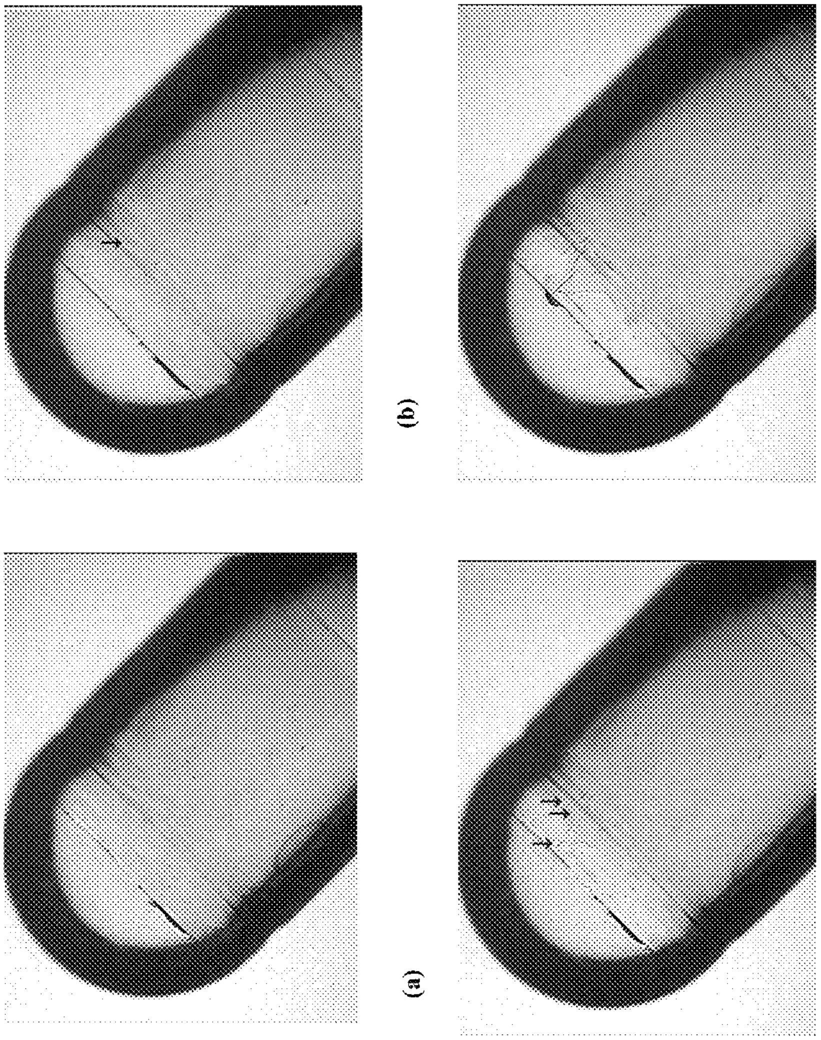
FIGS. 24*a-d* are magnified views of Qualicaps 00 clear capsule with DMA. Elapsed Time=90 seconds; (a) before cracking; (b) a crack initiates at the bottom of the cap locking ring groove; (c) Two cracks initiate at the transition corner between cap locking ring and the cap shoulder area. Another crack initiates at the shoulder area (d) cracks propagates upwards and downwards.
Figure 25:
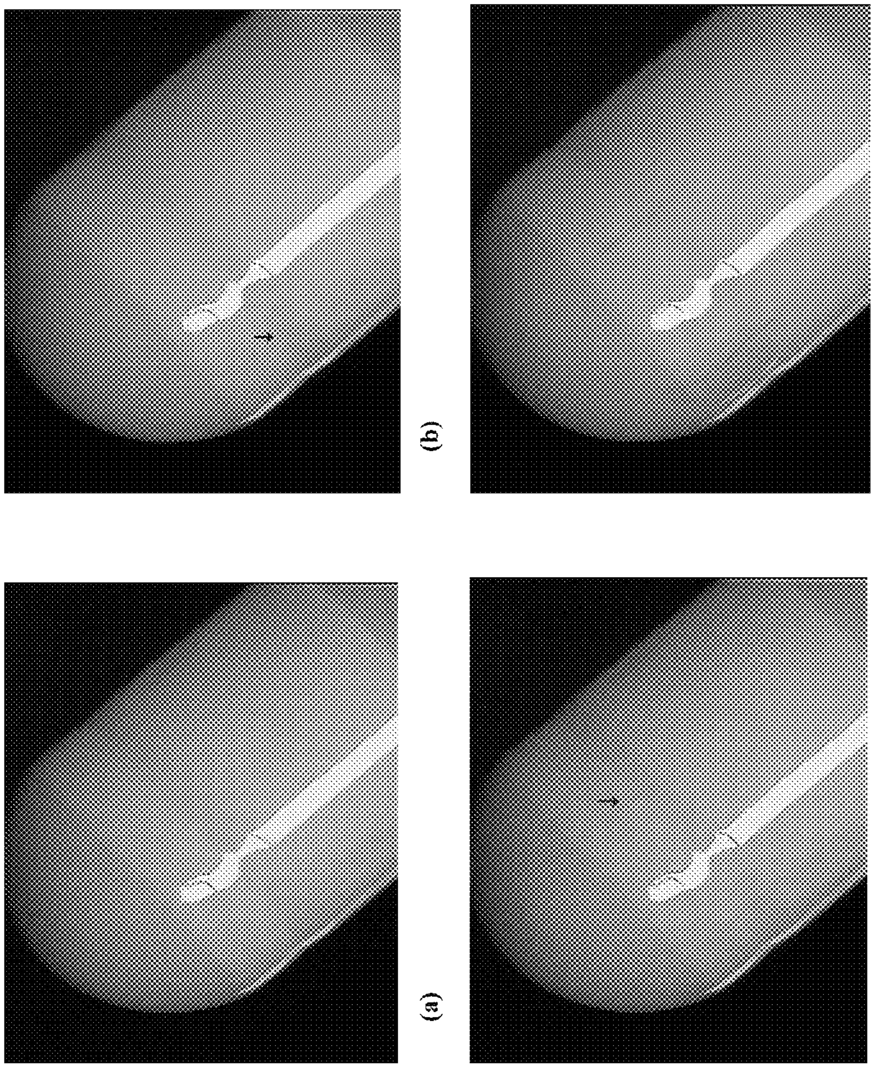
FIGS. 25*a-d* are magnified view of LICAPS® 0 opaque white with DMA filling. Elapsed time=30 seconds. (a) capsule before cracking; (b) the arrow indicates a crack initiates at the vertex of the angular locking ring area; (c) crack propagates and another crack initiates close to the first crack; (d) cracks propagate.

FIGS. 24 and 25 illustrate the observation that all the cracks are initiated at a high stress area and the areas with stress raisers. LICAPS® cracks all initiate at the vertex of the angular locking ring area. Qualicaps cracks initiate at three areas: the bottom of the locking ring, the juncture of the locking ring and the shoulder, and at the contact area of the body rim and cap shoulder. One common feature of these cracks is that all cracks formed longitudinally along the capsule. This is because the tensile stress is tangent to the capsule circumference. During the crack propagation, the direction can change depending on the tensile stress distribution.

Initially the inventors thought SuHeung will have a higher cracking rate compared to the other two vendor's capsules because SuHeung capsules have a relatively thinner shoulder area compared to Qualicaps or Capsugel. Usually thinner cap shoulders will crack easier, but conventional SuHeung capsules cracking rate is about 10%~40% with DMA filling, which is much lower compared to Qualicaps and LICAPS®.

Figure 26:
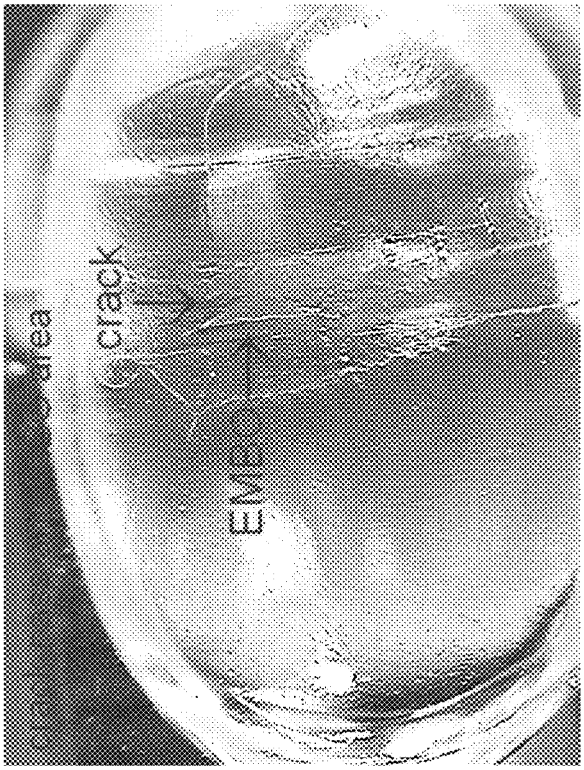
FIG. 26 is a magnified view of the SuHeung capsules illustrating the cracking in the EMBO® area.
Figure 27:
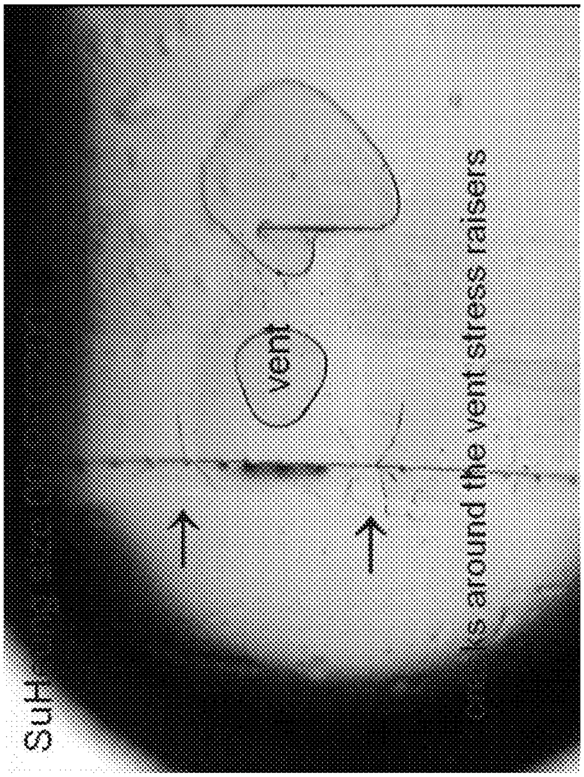
FIG. 27 is a magnified view of the SuHeung capsules illustrating the cracking at the corners of the body vents.

Although SuHeung capsules are less prone to cracking, when cracking did occur, it could be related back to definable design stress raisers. While some cracks were observed at the contact area of the body-rim and cap-shoulder area indicating there is some contact force between the body-rim and the cap-shoulder area, most cracks are around the EMBO® area (FIG. 26) because the EMBO® design is a stress raiser. Interestingly, no common straight crack in the locking ring area was found. This indicates the locking stress in SuHeung is very low and their locking ring design has lower stress compared to Capsugel or Qualicaps.

The following are data for LICAPS®, Qualicaps, and SuHeung size 00 clear capsules cracking rate after filling with PEG 400 and 200. Since PEG 400 is less hygroscopic than PEG 200, the inventors were able to see better resolution in the cracking process with PEG 400. Clearly from these data it can be seen that there are differences in performance between the different designs.

TABLE 2

| Capsule Type | Cracking Rate for PEG400 | Cracking Rate for PEG200 |
|---|---|---|
| LICAPS ® 00 | 65% | 100% |
| Qualicaps 00 | 55% | 100% |
| SuHeung 00 | 0% | *12% |

*There were some cracks in the shoulder area and some micro-cracks under the dimples. The cracks did not necessarily penetrate all the way through.

Again, most of the cracks observed occur at the locking ring for LICAPS® and POSILOK®. The locking ring is a stress raiser because it is a small irregular shaped area which disturbs the stress distribution throughout the shell. In addition, the locking ring area also sustains higher stress due to the locking force. Therefore, it becomes important that the locking ring area is designed to minimize both stress concentrations and locking force.

With SuHeung capsules, PEG caused cracks to initiate in three locations:

1. Around the EMBO® area.
2. Vent area.
3. Shoulder area (FIG. 28).

According to the previous analysis, EMBO® and vent areas form stress raisers. In addition, the shoulder area may have high contact force. These areas have relatively high tensile stress that can cause cracks. Interestingly, like was observed with DMA filling, no straight cracks initiated at the cap locking ring area. This indicates that there is a very low locking force on SuHeung capsules and the SuHeung locking ring design experiences less tensile stress than the others.

Figure 28:
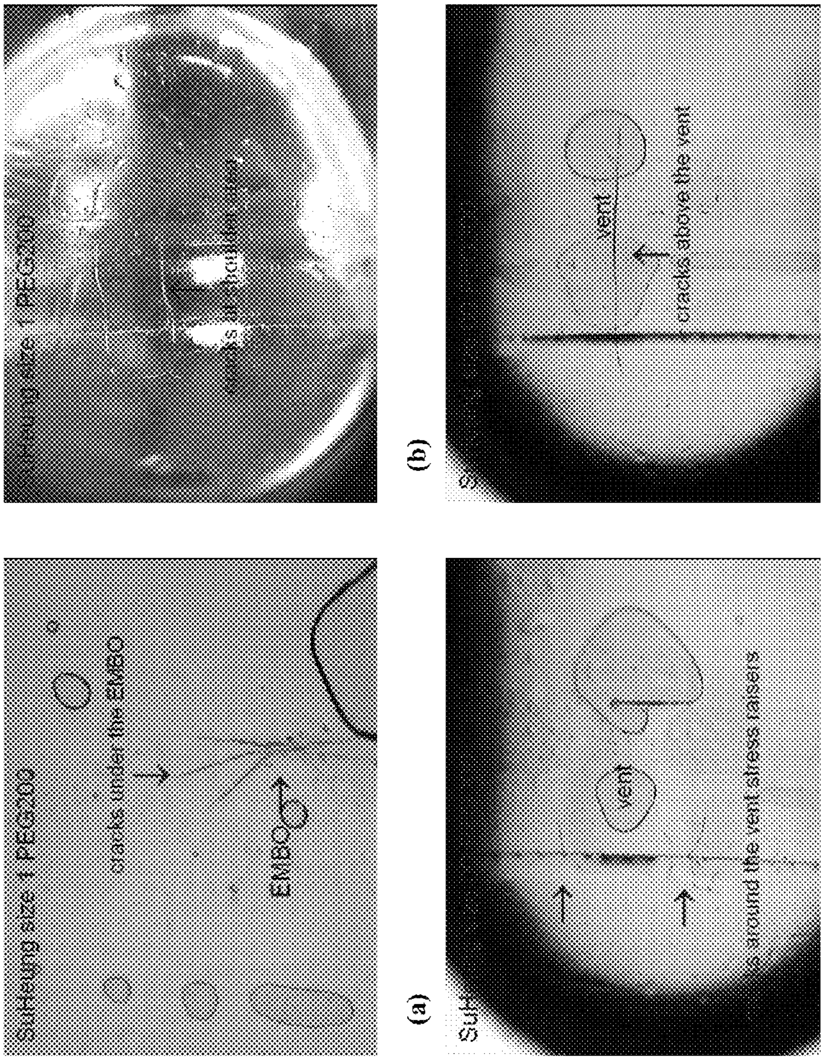
FIGS. 28*a-d* are magnified views of the SuHeung capsules showing cracking caused by PEG fill initiated at three locations: around the EMBO® area, vent area, shoulder area. a) micro cracks around an EMBO®; b) crack on shoulder area; c & d) cracks at the vent area.

FIG. 28 illustrates PEG caused SuHeung cracks initiate at three locations: around the EMBO® area, vent area, and shoulder area. a) micro cracks around an EMBO®; b) crack on shoulder area; c & d) cracks at the vent area.

Capsule Cracking Studies with Example Placebo Formulations

Four placebo formulations were made:

Formula 1:
94.8% PEG400
5.2% Povidone K-30

Formula 2:
91.8% PEG400
3.1% glycerin
5.1% povidone

Formula 3:
85% Capmul PG8
15% Capmul MCM-L

Formula 4:
90% PEG 600
10% ethanol

Formula 1 and 2 are common softgel example formulas without water or active material—water added in the softgel formulation to achieve a water balance between shell and fill and the shell may be specifically formulated for each fill material. Formulae 3 and 4 are placebo formulations. For each formulation these excipients were well mixed together at room temperature.

Four designs of Size 00 capsules from Qualicaps, Conventional SuHeung, Liquid fill SuHeung, and LICAPS® were filled with the four formulations. Then they were stored at RH-20% and RH-45%. For each design of capsule and formulation to be tested, twenty capsules were filled, ten for each humidity condition to be studied.

By the third day of testing, no cracks were found in capsules at low RH. The following test results (Table 3) were from capsules stored at high RH.

TABLE 3

Capsule cracking results from high humidity study (Target 45% RH):

| | Capsule | Day 1 | Day 3 |
|---|---|---|---|
| Formula 1 | Qualicaps | 0 | 0 |
| | liquid fill SuHeung | 5 fine cracks at vent | 7 fine cracks at vent |
| | conventional SuHeung | 0 | 0 |
| | LICAPS ® | 0 | 0 |
| Formula 2 | Qualicaps | 1 fine crack at locking ring | 1 fine crack at locking ring |
| | liquid fill SuHeung | 9 fine cracks at vent | 10 fine cracks at vent |
| | conventional SuHeung | 0 | 0 |
| | LICAPS ® | 1 body locking ring crack | 2 body locking ring crack |
| Formula 3 | Qualicaps | 1 body locking ring crack | 1 body locking ring crack |
| | liquid fill SuHeung | 10 fine cracks at vent, under EMBO ®, or at tight shoulder area | 10 fine cracks at vent, under EMBO ®, or at tight shoulder area |
| | conventional SuHeung | 6 very fine cracks under EMBO ®s | 7 very fine cracks under EMBO ®s |
| | LICAPS ® | 4 body locking ring cracks | 6 body locking ring cracks |
| Formula 4 | Qualicaps | 0 | 0 |
| | liquid fill SuHeung | 2 fine cracks at vent | 6 fine cracks at vent |
| | conventional SuHeung | 0 | 0 |
| | LICAPS ® | 0 | 0 |

Figure 29:
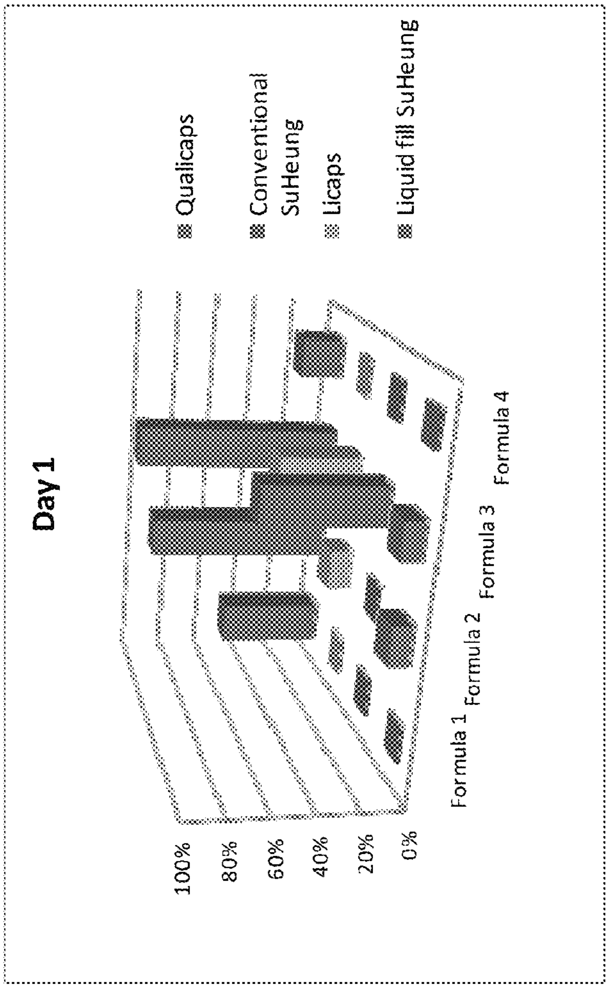
FIG. 29 demonstrates cracking of SuHeung capsules.
Figure 30:
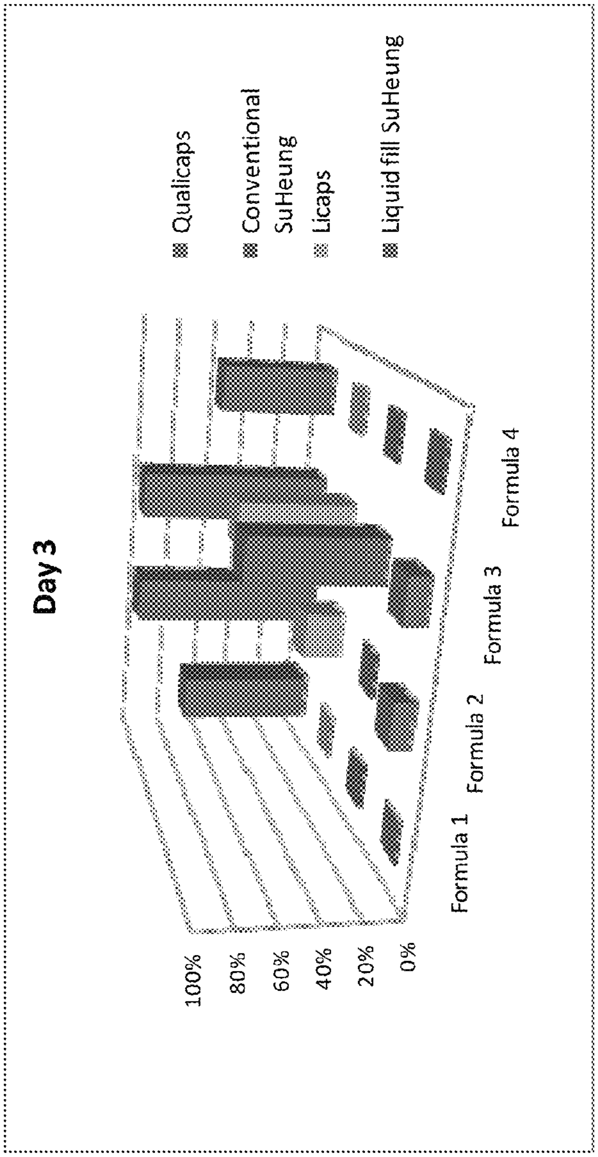
FIG. 30 demonstrates cracking of SuHeung capsules over an extended period of time.

It appears that Formulation 3 was the most aggressive in causing cracking. Capmul MCM-L is primarily Glycerol Monocaprylocaprate and Capmul PG8 is mainly Propylene Glycol Monocaprylate. However, there is a maximum of 7% free glycerol in Capmul MCM-L and a maximum of 1.5% free propylene glycol in Capmul PG8. Both glycerol and propylene glycol are very hygroscopic materials which can crack a capsule within one minute at high RH. The small amount of these hygroscopic ingredients in Capmul might be the reason for capsules cracking with Formulation 3. Formulation 4 is relatively weak because PEG600 is not a strong hydrophilic material. Alcohol will make the melting temperature lower, but it still didn't create cracks in low humidity environments. The other three formulas are similar PEG400 based formulas. Povidone makes the liquid thick, so the cracking rate would be expected to be lower for Formulations 1 and 2 compared to some previous pure PEG400 fill studies at similar humidity conditions. High viscosity components in liquid usually lower the hydrophilic molecular movement and concentration and this subsequently lowers the cracking rate. FIGS. 29 and 30 demonstrate that liquid fill SuHeung capsules have more cracks than the others. Conventional SuHeung capsules are preferred except their EMBO® design causes some very fine cracks under the EMBO®s. All these results are coherent with all previous test results.

Full Scale Studies with PEG400 and PEG300

Approximately 5000 capsules each from the following lots were used for PEG 400 study—including LICAPS® size 00, Qualicaps size 00, SuHeung size 00 (conventional design), and another liquid fill SuHeung 00 lot. Approximately 2000 capsules from each of these same lots were used for a subsequent study with PEG 300 fill material. Most often, the manufacturer increases the locking force for LFC capsules to resist leakage, but we believe this can create additional stress that leads to more cracking. Capsules were filled using a LIQFIL Super 40 filler at a speed of 20,000 caps/hr. After filling, capsules were banded using a HICAPSEAL 40 bander with gelatin banding solution. The testing temperature was ~74 F.° and RH was 40~44%.

For the PEG400 study, it was observed that some capsules had the typical shoulder-locking ring area cracks after two days. At the beginning of this study, the filled capsules were left at an RH that was relatively low (about 41~44%) and very stable, so the cracking rate was low. After seven days, all the capsules were moved to a RH of about 35% and no more new cracks were found. To better study capsule cracking conditions, after eight days, half of the capsules were moved to a RH to above 60%. The other half of the capsules were still maintained at low humidity. The results from this study are summarized below:

At an RH of about 40%, there was no further capsule cracking for any of the different lots. In this run, about 10~20 leaking or cracked capsules per tray were found for the liquid fill SuHeung capsules. About 2~5 leaking capsules per tray were found in the Qualicaps capsules. LICAPS® had only about 1 leaking capsule per tray. And there were no leaking capsules among the conventional SuHeung capsules. Besides the leaking capsules, some non-leaking capsules were also examined under the microscope and fine shoulder and locking ring area cracks were found on almost all the liquid fill SuHeung capsules and some Qualicaps and LICAPS® capsules, but they didn't cause leaking at this point. These fine cracks may propagate and start leaking in the future. Interestingly, no fine cracks were found on the conventional SuHeung capsules. All the capsule cracking patterns are the same as noted in previous lab scale studies. The only difference was the cracking rate. In both the PEG400 and PEG300 full scale studies, cracking rates were lower as compared to the earlier lab studies. This will be discussed in the next section.

PEG300 full scale testing results were similar to the PEG400 study because PEG300 is not significantly more hygroscopic compared to PEG 400. At RH 43~51%, no leaking capsules were found for either the LICAPS® or conventional SuHeung capsules. 1~2 leaking capsules per tray were found for the Qualicaps, and 15~18 leaking capsules per tray were found for liquid fill SuHeung capsules. All the cracking patterns were comparable to the PEG400 study. The reason for the relatively lower cracking rate most likely because the RH was lower than it was during the PEG400 study (RH>60%). When RH was subsequently increased to over 60% for 2 days, the leakage rate for the liquid fill SuHeung capsules increased to over 50 capsules per tray. Both Qualicaps and LICAPS® leaking rates increased to about 10~20 capsules per tray. No leaking capsules were found among the conventional SuHeung capsules.

There is a significant difference in that the conventional SuHeung had no cracks but the liquid fill SuHeung had the most cracks. (In previous DMA and PEG lab studies, convention) SuHeung capsules were used. It is believed that is a reason why the lowest cracking rate among three capsules consistently was obtained with SuHeung in all previous studies.) The only difference known now is the pin design difference. Under microscopic examination, it was noted that the liquid fill SuHeung has a very tight shoulder area with a sharp turn design. The tight shoulder area makes the cap shoulder sustain high tensile stress after capsule closing and the sharp turn design as a stress raiser will make the stress even higher at the shoulder area. This is one reason for the high cracking rate.

For microscopic observation, some capsules were longitudinally cross sectioned and viewed under magnification. On the cap part, the difference noted was at the shoulder area. The liquid fill SuHeung caps have a bump design between the shoulder and the locking ring. All the cracks initiate at the shoulder area close to the bump, not at the locking ring area like for other capsules.

Based on these observations and tests, the inventors postulate that the capsule cracking can be related to tensile stresses that occur as a combined result of physiochemical stresses caused by the fill interacting with the shell and design attributes of the capsules that either add additional tensile stress, or that form stress raisers that lead to tensile stress increase around the stress raisers. The locking force experienced at the locking ring of the capsule is a major stress contributor leading to capsule failure.

Analysis of the cracking patterns identified above indicates that cracks in the capsule may be avoided by avoiding the stress raisers.

Comparison of Full Scale Study with a Lab Scale Study

One difference between the previous lab scale study and the full scale study is that the leaking capsule rate in the full scale study is lower than the previous lab scale study. It is believed that this can be explained by the difference in the RH in the two studies.

RH and temperature in the manufacturing area was more stable compared to the laboratory that was used for the initial study. In the manufacturing area, the temperature was consistently around 74 F.° and the RH was about 40~44%. Data over extended time periods showed very little change. At this RH, capsules do not easily crack with PEG 300 and PEG 400 fill materials, but in the lab there was more temperature and RH change on a daily base. In summer, usually at night time the RH is higher. Sometimes the RH can reach over 60~80% at night time and over 50% during the days from June to August. Many of the previous lab studies were performed during that timeframe. This helps to explain the high cracking rate in the previous study.

PEG300 and PEG400 lab scale studies were conducted at RH 45~51% and RH 23~26%. Four capsule designs were examined including the same LICAPS®, Qualicaps, liquid filled SuHeung, and conventional SuHeung lots used in the full scale study. The results are presented in Table 4.

TABLE 4

| | RH 45~51% | | RH 23~26% | |
|---|---|---|---|---|
| Capsule Type | Cracking Rate for PEG300 | Cracking Rate for PEG400 | Cracking Rate for PEG300 | Cracking Rate for PEG400 |
| LICAPS ® 00 | 3/10 | 1/10 | 0/10 | 0/10 |
| Qualicaps 00 | 1/10 | 0/10 | 0/10 | 0/10 |
| liquid filled SuHeung 00 | 0/10 | 0/10 | 0/10 | 0/10 |
| conventional SuHeung 00 | 8/10 | 8/10 | 0/10 | 0/10 |

Only fine cracks were found on the capsules stored at RH 45%. No crack size big enough to cause leaking was found. No cracks were found on the conventional SuHeung, but the liquid fill SuHeung had the most cracks. No cracks were found on any of the capsules stored at RH 23%, where capsules were stored at lower humidity. The cracking rate observed with those capsules was much lower compared to the previous results in Table 2. The capsule cracks in Table 2 were all big cracks causing capsule leaking except for on the SuHeung capsules. The RH dramatically affected the capsule cracking condition because, at low RH, the shrinkage difference between the capsule outside layer and inside layer is small, so the tensile stress inside the capsule shell is low. The crack patterns are the same as in all the previous studies.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A gelatin capsule comprising a body portion and a cap portion:

- the body portion having an open top including a tapered rim, shoulder area and a closed rounded bottom;
- the cap portion having a closed rounded top, a shoulder area and open bottom, the top portion dimensioned and configured to fit over the body portion to comprise a closed capsule;
- wherein the tapered rim is dimensioned and configured such that when the cap is secured, the rim does not contact the cap portion;
- wherein the body portion further includes a first part of a locking ring comprising an annular groove around the circumference of the body portion;
- wherein the cap portion includes a second part of the locking ring comprising an annular ring around the circumference of the cap portion, the annular ring dimensioned and configured to matingly engage the annular groove on the body portion;
- wherein the dimension of the annular ring of the cap portion has a radius and width less than the dimension of the annular groove on the body portion such that the annular ring of the cap portion freely nests inside the annular groove of the body portion when the cap portion is sealed on the body portion.

2. The gelatin capsule of claim 1, wherein the height of the annular ring of the cap portion is equal to or greater than the depth of the annular groove of the body portion.

3. The gelatin capsule of claim 2, wherein the annular ring of the cap portion is between about 0.05 mm to 0.15 mm high and the annular groove of the body portion is between about 0.03 to 0.14 mm deep.

4. The gelatin capsule of claim 2, wherein the width of the annular groove of the body portion is between about 2.0 mm to about 6.0 mm and the width of the annular ring of the cap portion is between about 1.0 mm to about 5.0 mm.

5. The gelatin capsule of claim 4, wherein the radius of the annular ring of the cap portion is 1.5 mm to 4 mm and the radius of the annular groove of the body portion 2 mm to 5 mm.

6. The gelatin capsule of claim 1, further comprising: a shoulder between the rounded top and the annular ring of the cap portion.

7. The gelatin capsule of claim 6, wherein the length of the shoulder of the cap portion is between 0.2 mm to 1.2 mm, and the inner diameter of cap straight shoulder area is same as the outer diameter of body shoulder area.

8. The gelatin capsule of claim 6, wherein the shoulder is straight.

9. The gelatin capsule of claim 1, wherein the tapered rim of the body portion has a bevel angle of from about 4° to 10°.

10. The gelatin capsule of claim 1, wherein the tapered rim of the body portion has a bevel length from 0.5 mm to 1.5 mm.

11. The gelatin capsule of claim 1, wherein the cap thickness is from 0.09 mm to 0.2 mm.

12. The gelatin capsule of claim 1, wherein the body portion has a thickness of from about 0.06 mm to about 0.15 mm.

13. The gelatin capsule of claim 6, further comprising: round junctions connecting the annular groove of both body and cap portion and cylinder area of both cap and body, the straight shoulder area of both body and cap portion and the annular groove of both body and cap portion.

14. The gelatin capsule of claim 13, wherein the round junction has a radius between 0.1 mm to 1 mm.

15. The gelatin capsule of claim 1, further comprising: one or more dimples in the cap between the rim and the locking ring dimensioned and configured to matingly engage with the annular ring of the body portion and defining a half-locked position.

16. A gelatin capsule for a hygroscopic material comprising:

- (i) a body portion comprising: an open top having a tapered rim, a shoulder area, and a closed rounded bottom, and a first portion of a locking ring comprising an annular groove;
- (ii) a cap portion comprising: a closed top, a shoulder area, a second portion of a locking ring comprising an annular ring;
- (iii) the locking ring further comprising the annular groove that has a greater radius and width than the annular ring and the annular ring height is greater than the depth of the annular groove.

17. The gelatin capsule of claim 16, wherein the annular ring of the cap portion is between about 0.05 mm to 0.15 mm in height and the annular groove of the body portion is between about 0.03 to 0.14 mm in depth.

18. The gelatin capsule of claim 16, wherein the width of the annular groove of the body portion is between about 2.0 mm to about 6.0 mm.

19. The gelatin capsule of claim 16, wherein the width of the annular ring of the cap portion is between about 1.0 mm to about 5.0 mm and is less than the width of the annular groove.

20. The gelatin capsule of claim 16, wherein the radius of the annular ring of the cap portion is 1.5 mm to 4 mm and the radius of the annular groove of the body portion 2 mm to 5 mm and the radius of the annular ring and the annular groove are not equal.

21. The gelatin capsule of claim 16, wherein the shoulder area of both the cap portion and the body portion is straight.

22. The gelatin capsule of claim 21, wherein the shoulder length of the cap portion is between 0.2 mm to 1.2 mm, and the inner diameter of cap shoulder area is same as the outer diameter of body shoulder area.

23. The gelatin capsule of claim 16, wherein the tapered rim of the body portion has a bevel angle of from about 4° to 10°.

24. The gelatin capsule of claim 16, wherein the tapered rim of the body portion has a bevel length from 0.5 mm to 1.5 mm.

25. The gelatin capsule of claim 16, wherein the cap thickness is from 0.09 mm to 0.2 mm.

26. The gelatin capsule of claim 16, further comprising: one or more dimples in the cap between the rim and the locking ring dimensioned and configured to matingly engage with the annular ring of the body portion and defining a half-locked position.

27. A locking ring for a gel capsule comprising:

an annular groove on a first portion of the gel capsule; and an annular ring on a second portion of the gel capsule;

wherein the annular ring on the second portion has a radius and width smaller than the annular groove on the first portion such that the annular ring of the second portion freely nests inside the annular groove of the first portion when the second portion is sealed on the first portion;

the annular groove and the annular ring designed and configured to matingly engage with a locking force of about 50 MPa to about 5 MPa.

28. The locking ring of claim 27, wherein the locking force is between about 25 MPa to about 10 MPa.

29. The locking ring of claim 27, wherein the locking force results from a differential in the diameter of the first portion to the second portion of between about 0.10% and 0.50%.

30. The locking ring of claim 29, wherein the differential in the diameter of the first portion to the second portion is about 0.25%.

31. The locking ring of claim 27 wherein the locking force results from the annular ring on the second portion having a width equal to or smaller than the annular groove on the first portion such that the annular ring nests inside the annular groove.

32. The locking ring of claim 27, wherein the height of the annular ring is the equal to or greater than the depth of the annular groove.

* * * * *